US010280199B2

(12) United States Patent
Kim

(10) Patent No.: US 10,280,199 B2
(45) Date of Patent: May 7, 2019

(54) CORONAVIRUS PROTEINS AND ANTIGENS

(71) Applicant: Phibro Animal Health Corporation, Teaneck, NJ (US)

(72) Inventor: Byoung-Kwan Kim, Mankato, MN (US)

(73) Assignee: Phibro Animal Health Corporation, Teaneck, NJ (US)

( * ) Notice: Subject to any disclaimer, the term of this patent is extended or adjusted under 35 U.S.C. 154(b) by 51 days.

(21) Appl. No.: 15/228,898

(22) Filed: Aug. 4, 2016

(65) Prior Publication Data

US 2016/0339097 A1    Nov. 24, 2016

Related U.S. Application Data

(63) Continuation-in-part of application No. PCT/US2015/015009, filed on Feb. 9, 2015, and a continuation-in-part of application No. PCT/US2016/017183, filed on Feb. 9, 2016.

(60) Provisional application No. 61/937,419, filed on Feb. 7, 2014, provisional application No. 62/209,538, filed on Aug. 25, 2015, provisional application No. 62/113,976, filed on Feb. 9, 2015, provisional application No. 62/113,979, filed on Feb. 9, 2015.

(51) Int. Cl.
| C07K 14/005 | (2006.01) |
| A61K 39/12 | (2006.01) |
| A61K 39/00 | (2006.01) |

(52) U.S. Cl.
CPC ............ *C07K 14/005* (2013.01); *A61K 39/12* (2013.01); *A61K 2039/552* (2013.01); *C12N 2770/20011* (2013.01); *C12N 2770/20034* (2013.01); *C12N 2770/20051* (2013.01); *C12N 2770/20071* (2013.01)

(58) Field of Classification Search
CPC .................. C07K 16/10; A61K 39/215; A61K 2039/552; A61K 2039/70; C12N 2770/10064; C12N 2770/20011; G01N 2333/165; C07D 211/62; Y10T 436/24
See application file for complete search history.

(56) References Cited

U.S. PATENT DOCUMENTS

| 7,241,582 B2* | 7/2007 | Joo ...................... C07K 14/005 435/7.4 |
| 7,449,296 B2 | 11/2008 | Jung |
| 7,776,537 B2* | 8/2010 | Joo ...................... C07K 14/005 435/6.16 |
| 8,142,788 B2 | 3/2012 | Kim |
| 9,388,218 B2* | 7/2016 | Joo ...................... C07K 14/005 |
| 9,950,061 B2* | 4/2018 | Hernandez .............. C07K 16/10 |
| 2005/0220814 A1 | 10/2005 | Dominowski et al. |
| 2011/0038900 A1 | 2/2011 | Chakrapani et al. |
| 2011/0177116 A1 | 7/2011 | Wasmoen et al. |
| 2013/0302370 A1 | 11/2013 | Fachinger et al. |
| 2014/0004041 A1 | 1/2014 | Bey et al. |
| 2014/0179594 A1 | 6/2014 | Fischetti et al. |
| 2014/0255442 A1 | 9/2014 | Burgard et al. |
| 2015/0283229 A1 | 10/2015 | Hernandez et al. |

FOREIGN PATENT DOCUMENTS

| WO | WO 2002/074940 | 9/2002 |
| WO | WO 2003/096463 | 11/2003 |
| WO | WO 2007/00006031 | 1/2007 |

OTHER PUBLICATIONS

International Search Report dated May 22, 2015, from International Application No. PCT/US2015/015009.
International Search Report dated Jul. 26, 2016, from International Application No. PCT/US2016/017183.
Lawrence et al., "Genome sequences of porcine epidemic diarrhea virus: in vivo and in vitro phenotypes," *Genome Announcements* 2(3):1-2, May/Jun. 2014, Jun. 12, 2014.
Oh et al., "Comparison of an enzyme-linked immunosorbent assay with serum neutralization test for serodiagnosis of porcine epidemic diarrhea virus infection," *Journal of Veterinary Science* 6(4):349-352, Dec. 1, 2005.
Song et al., "Porcine epidemic diarrhoea virus: a comprehensive review of molecular epidemiology, diagnosis, and vaccines," *Virus Genes* 44(2):167-175, Jan. 22, 2012.
Takamura et al., "Protection studies on winter dysentery caused by bovine coronavirus in cattle using antigens prepared from infected cell lysates," *Canadian Journal of Veterinary Research* 64:138-140, Apr. 1, 2000.
Takamura et al., "Field study of bovine coronavirus vaccine enriched with hemagglutinating antigen for winter dysentery in dairy cows," *Canadian Journal of Veterinary Research* 66:278-281, Oct. 1, 2002.
Chen et al., "Method for obtaining membrane protein involves infecting animal host cells with rhabdovirus Bacmid CMV-G-HA, forming cyst membrane utilizing host cell substances during budding of virus, separating virion and freeze thawing," Derwent No. 2009-E71195, Derwent Abstract of CN 101348800 published Jan. 21, 2009.
Di-qiu et al., "High-level mucosal and systemic immune responses induced by oral administration with *Lactobacillus*-expressed porcine epidemic diarrhea virus (PEDV) S1 region combined with *Lactobacillus*-expressed N protein," *Applied Genetics and Molecular Biotechnology* 93(6): 2437-2446, 2012.

(Continued)

*Primary Examiner* — Bao Q Li
(74) *Attorney, Agent, or Firm* — Klarquist Sparkman, LLP

(57) ABSTRACT

Disclosed herein are embodiments of a method for collecting, extracting or eluting proteins and antigens from cells infected with coronavirus. The coronavirus may be a porcine coronavirus, such as porcine epidemic diarrhea virus (PEDV) or porcine delta coronavirus (PDCoV). Also disclosed are embodiments of a composition comprising the coronavirus proteins and antigens, and embodiments of a method of using such a composition. Applications for the composition include, but are not limited to, use in the preparation of antibodies against the proteins and antigens, use as reference markers for coronavirus proteins, and/or use in an immunogenic composition, such as in a vaccine composition.

20 Claims, 11 Drawing Sheets

Specification includes a Sequence Listing.

(56) References Cited

OTHER PUBLICATIONS

Egberink et al., "Characterization of the structural proteins of porcine epizootic diarrhea virus, strain CV777," *American Journal of Veterinary Research*, 49(8):1320-1324, Aug. 1988.
Hernandez et al., "Porcine epidemic diarrhea virus derived DNA (45-28031)," Sequence alignment of nt 20000-24000 of SEQ ID No. 1 with Geneseq Database Access No. BCF33575.
Park et al., "Receptor-bound porcine epidemic diarrhea virus spike protein cleaved by trypsin induces membrane fusion," *Archives of Virology* 156:1749-1756, 2011.
Shaikh et al., "Mucoadhesive drug delivery systems," *Journal of Pharmacy and Bioallied Sciences*, 3(1):89-100, Jan.-Mar. 2011.
Song et al., "Oral efficacy of Vero cell attenuated porcine epidemic diarrhea virus DR13 strain," *Research in Veterinary Science* 82:134-140, 2007.

* cited by examiner

|  | Born alive (litter average) | Pigs remaining at weaning (litter average) | Piglet mortality |
| --- | --- | --- | --- |
| Vaccinated sows – 10hd – 2cc dose | 133 (13.3) | 113 (11.3) | 15% |
| Non-vaccinated sows – 33hd | 405 (12.2) | 291 (8.8) | 28% |

FIG. 3

|  | # litters | Born alive (litter average) | Pigs weaned (litter average) | Pre-weaning mortality |
|---|---|---|---|---|
| Entire rooms vaccinated | 128 | 1466 (11.4) | 1324 (10.3) | 9.6% |
| No vaccine used in rooms | 88 | 1059 (12.0) | 872 (9.9) | 17.6% |

FIG. 4

|  | Farm 1 | Farm 2 | Farm 3 | Farm 4 | Farm 5 | Farm 6 | All farm average |
|---|---|---|---|---|---|---|---|
| Day 1-7 | 100 | 99 | 97 | 100 | 97 | 100 | 98% |
| Day 8-15 | 98 | 94 | 98 | 98 | 100 | 100 | 98% |
| Day 16-23 | 51 | 47 | 78 | 89 | 90 | 100 | 76% |
| Day 24-31 | 23 | 24 | 34 | 54 | 45 | 100 | 46% |
| Day 32-39 | 19 | 14 | 27 | 43 | 34 | 100 | 39% |
| Day 40-47 | 19 | 25 | 17 | 30 | 16 | 22 | 21% |
| Day 48-55 | 24 | 12 | 18 | 27 | 20 | 37 | 23% |
| Day 56-63 | 19 | 11 | 16 | 25 | 19 | 32 | 20% |
| Individual farm average prior to PEDV | 15% | 14% | 15% | 20% | 17% | 12% | |

FIG. 5

Case 1  Case 2  Case 3  Case 4
Std S P P P S P P P S P P P S P P P kDa
220 --
120 --

Std, Protein Molecular Weight Standard
S, Sow serum samples
P, Piglet serum samples

1. 2x diluted sample
2. 3x diluted sample
3. 4x diluted sample
4. Fully grown virus culture itself
S. SeeBlue Protein MW Standard
M. Magic Protein MW Standard
CO. PEDv isolate from sample taken in Colorado
IA. PEDv isolate from sample taken in Iowa
NC. PEDv isolate from sample taken in North Carolina

FIG. 7

1. DE sample from CO-virus culture
2. DE sample from IA-virus culture
3. DE sample from NC-virus culture
4. Mix of 3 DE samples before inactivation process
5. Mix of 3 DE samples after inactivation process
6. Mix of 3 virus cultures in equal volume
S. SeeBlue Protein MW Standard
M. Magic Protein MW Standard

CORONAVIRUS PROTEINS AND ANTIGENS

CROSS REFERENCE TO RELATED APPLICATION

This application is a continuation-in-part of International Application No. PCT/US2015/015009, filed on Feb. 9, 2015, which in turn claims the benefit of the earlier filing date of U.S. Provisional Patent Application No. 61/937,419, filed on Feb. 7, 2014. This application also claims the benefit of the earlier filing date of U.S. Provisional Patent Application No. 62/209,538, filed on Aug. 25, 2015, and of International Application No. PCT/US2016/017183, filed on Feb. 9, 2016, which in turn claims the benefit of the earlier filing dates of U.S. Provisional Patent Application Nos. 62/113,976 and 62/113,979, both filed on Feb. 9, 2015. Each of these applications is incorporated by reference herein in its entirety.

FIELD

This disclosure relates to the preparation and isolation of coronavirus proteins and antigens, particularly from porcine coronaviruses. The disclosure further provides viral proteins and antigens as obtained from coronavirus infected cells and compositions comprising the proteins and antigens.

BACKGROUND

Coronaviruses are a family of RNA viruses that infect avians and mammals, including humans and swine. Coronaviruses belong to the family Coronaviridae, which has four main sub-groupings, known as alphacoronavirus, betacoronavirus, gammacoronavirus and deltacoronavirus. Human coronaviruses include alphacoronaviruses 229E and NL63, and betacoronaviruses OC43, HKU1, SARS-CoV (the coronavirus that causes severe acute respiratory syndrome, or SARS), and MERS-CoV (the coronavirus that causes Middle East Respiratory Syndrome, or MERS). Porcine coronaviruses include alphacoronaviruses, such as transmissible gastroenteritis virus, porcine respiratory coronavirus, and porcine epidemic diarrhea virus (PEDV); betacoronaviruses, such as porcine hemagglutinating encephalomyelitis virus; and deltacoronavirus, such as porcine deltacoronavirus (PDCoV). Other coronaviruses include, but are not limited to, bovine coronavirus (BCV), feline coronavirus (FCoV), canine coronavirus (CCoV), avian infectious bronchitis virus (IBV), and turkey coronavirus (TCV). Porcine coronaviruses are important diseases in swine production. For example, PEDV is a highly infectious coronavirus that infects the intestinal system of a pig, typically causing diarrhea and dehydration. While adult pigs mostly become sick and lose weight after becoming infected, the virus is often fatal to newborn piglets. Infected herds can suffer a loss of from 50% to 100% of the piglets for a four to five week period. It has been estimated that between June 2013 and March 2014 over 4 million piglets were lost to PEDV in USA.

SUMMARY

This disclosure relates to proteins and antigens from a coronavirus. The coronavirus can be any coronavirus currently known, or later discovered. In certain embodiments, the disclosure relates to coronaviruses that infect avian or mammals, including, but not limited to, humans, and swine. The coronavirus may be a porcine coronavirus, and may be selected from transmissible gastroenteritis virus, porcine respiratory coronavirus, PEDV, porcine hemagglutinating encephalomyelitis virus, or PDCoV. Particular embodiments concern proteins and antigens from PEDV, and other particular embodiments concern proteins and antigens from PDCoV.

Disclosed herein are embodiments of a method of preparing coronavirus proteins and/or antigens, such as PEDV or PDCoV proteins and/or antigens, from cells infected with a coronavirus, such as PEDV or PDCoV. In some embodiments, the proteins and/or antigens are harvested at an early time point after infection when the majority, or entirety, of the viral proteins and/or antigens remain associated with the infected cells. In such embodiments, the majority or entirety of coronavirus encoded proteins are either within the infected cells or associated with the cell membrane of the infected cells. Under such conditions, relatively few, if any, coronavirus particles are present in the extracellular environment outside the cells. In other embodiments, the proteins and/or antigens are harvested at a stage after infection when at least some of the infected cells have released replicated coronavirus viral particles into the extracellular environment.

Certain embodiments of the disclosed method may include providing a population of cultured cells infected with a coronavirus, such as PEDV or PDCoV; isolating and/or separating the coronavirus-infected cells from the culture medium and/or cell-free coronavirus in the medium; and collecting coronavirus proteins and/or antigens from the isolated cells. Collecting viral proteins and/or antigens may be done by extracting or eluting them from the isolated, infected cells with a detergent-containing solution. In some examples, the detergent-containing solution comprises an amount of detergent effective to extract or elute the proteins and/or antigens, such as 0.5% Triton X-100. In additional embodiments, the collecting, extracting or eluting may be for up to 24 hours, such as 2 to 15 hours or in some embodiments, from 0.2 to 5 hours. The collecting, extracting or eluting is performed at a temperature suitable for the collecting, extracting or eluting, such as from 0° C. to 25° C., from 2° C. to 10° C., from 2° C. to 6° C. or, in certain examples, 4° C. Optionally, the coronavirus proteins and/or antigens produced by the method may include coronavirus envelope proteins, such as PEDV envelope proteins or PDCoV envelope proteins.

Also disclosed herein are isolated coronavirus proteins and/or antigens, such as PEDV or PDCoV proteins and/or antigens, prepared by the disclosed method. The viral proteins and/or antigens may include one or more envelope proteins produced by an infected cell. Compositions comprising the viral proteins and/or antigens are also contemplated. Optionally, the composition may contain one or more adjuvants, and/or additional excipients, such as a pharmaceutically acceptable carrier.

Embodiments of a method of producing an immune response in a subject, such as a porcine subject, are also disclosed. The method may include administering one or more coronavirus proteins and/or antigens, prepared by the disclosed method, to the subject. The one or more coronavirus proteins and/or antigens may comprise one or more proteins and/or antigens from a single coronavirus. Additionally, or alternatively, the one or more coronavirus proteins and/or antigens may comprise proteins and/or antigens from one or more coronaviruses, such as, for example, PEDV and PDCoV. In certain embodiments, the method comprises administering one or more PEDV or PDCoV proteins and/or antigens to a porcine subject. Optionally, producing an immune response may comprise vaccinating the subject. In some embodiments, a composition comprising the proteins and/or antigens is administered to the subject. The method may also include one or more repeated administration(s) of the proteins and/or antigens, or the composition, to the same subject, such as 2, 3, 4 or more administrations.

Embodiments of a kit comprising the isolated proteins and/or antigens is disclosed herein. The kit may comprise a composition comprising the coronavirus proteins and/or antigens. In some embodiments, the kit is suitable for use in a method of producing an immune response in, or a method of vaccinating, a subject.

The various aspects of the disclosure are contemplated for use in relation to all coronavirus strains that are antigenically identical, or related to, those isolated in North America, Europe and Asia. Therefore, the disclosure may be more generally viewed as based on the protein(s) and/or antigens of any coronavirus isolate, strain or subtype.

The foregoing and other objects, features, and advantages of the invention will become more apparent from the following detailed description, which proceeds with reference to the accompanying figures.

BRIEF DESCRIPTION OF THE DRAWINGS

FIG. 3 is a table of data comparing the mortality of piglets from non-vaccinated sows and sows vaccinated 3-5 days pre-farrow with an exemplary embodiment of a PEDV vaccine disclosed herein, where the non-vaccinated and vaccinated sows and litters are kept in the same room.

FIG. 4 is a table of data comparing the mortality of piglets from non-vaccinated sows and sows vaccinated 3-5 days pre-farrow with an exemplary embodiment of a PEDV vaccine disclosed herein, where the non-vaccinated and vaccinated sows and litters are kept in separate rooms.

FIG. 5 is a table of data from multiple farms, providing baseline piglet mortality data from non-vaccinated herds.

FIG. 6 is a Western blot illustrating the detection of antibodies against 180-kDa to 350-kDa of PEDV spike protein.

FIG. 7 is a Western blot of three MARC-cell based detergent extracts of PEDV isolates, illustrating the proteins present in the extracts.

FIG. 8 is a Western blot of the three detergent extracts of FIG. 7 and mixtures of the extracts before and after viral inactivation, illustrating the proteins present before and after inactivation.

FIG. 9 is a table illustrating the PEDV sequence homology between SEQ ID NOS: 1-9.

FIGS. 10A-10C are tables illustrating the PDCoV sequence homology between SEQ ID NOS: 18-63.

FIG. 10A is a table illustrating the PDCoV sequence homology concerning 15 strains.

FIG. 10B is a table illustrating the PDCoV sequence homology concerning another 15 strains.

FIG. 10C is a table illustrating the PDCoV sequence homology concerning another 16 strains.

SEQUENCE LISTING

Figure 1:
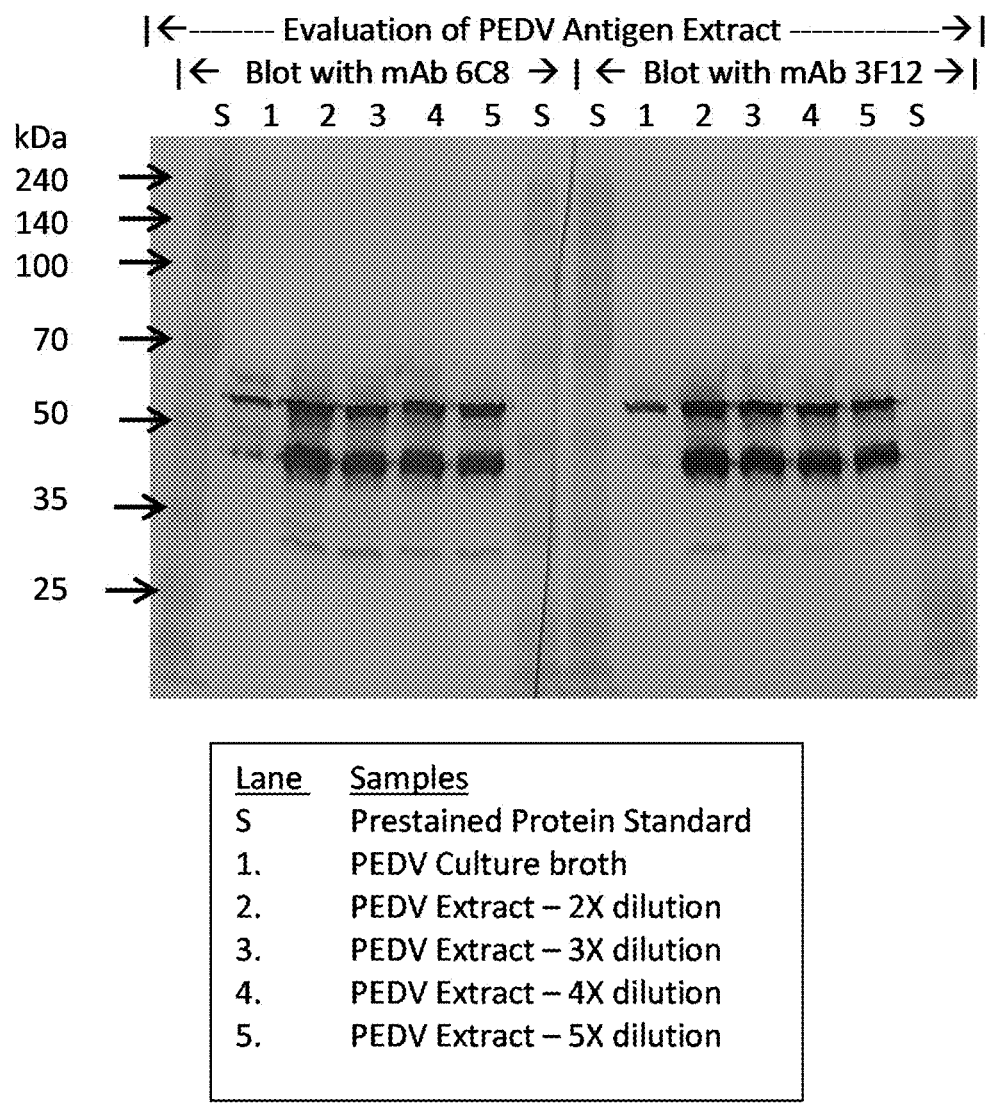
FIG. 1 is a Western blot of PEDV proteins from cultures of infected cells, contacted with two monoclonal antibodies.

The nucleic and amino acid sequences listed in the accompanying sequence listing are shown using standard letter abbreviations for nucleotide bases, and three letter code for amino acids, as defined in 37 C.F.R. § 1.822. Only one strand of each nucleic acid sequence is shown, but the complementary strand is understood as included by any reference to the displayed strand. The Sequence Listing is submitted as an ASCII text file, created on Aug. 4, 2016, 1.86 MB, which is incorporated by reference herein. In the accompanying sequence listing:

SEQ ID NO: 1 is the nucleotide sequence of North American PEDV strain Colorado 2013 (GenBank Accession No. KF272920).

SEQ ID NO: 2 is the nucleotide sequence of North American PEDV strain Iowa/18984/2013 (GenBank Accession No. KF804028).

SEQ ID NO: 3 is the nucleotide sequence of North American PEDV strain North Carolina USA/NC/2013/35140 (GenBank Accession No. KM975735).

SEQ ID NO: 4 is the nucleotide sequence of North American PEDV strain Indiana12.83/2013 (GenBank Accession No. KJ645635).

SEQ ID NO: 5 is the nucleotide sequence of North American PEDV strain Iowa/2013 (GenBank Accession No. KJ645649).

SEQ ID NO: 6 is the nucleotide sequence of North American PEDV strain 1251-125-10.

SEQ ID NO: 7 is the nucleotide sequence of Korean PEDV strain SM98 (GenBank Accession No. GU937797).

SEQ ID NO: 8 is the nucleotide sequence of Korean attenuated PEDV strain KR-DR13-att (GenBank Accession No. JQ023162).

SEQ ID NO: 9 is the nucleotide sequence of Chinese PEDV strain AH2012 (GenBank Accession No. KC210145).

SEQ ID NO: 10 is the deduced amino acid sequence of the S protein encoded by SEQ ID NO: 1 North American PEDV strain Colorado 2013.

SEQ ID NO: 11 is the deduced amino acid sequence of the S protein encoded by SEQ ID NO: 2 North American PEDV strain Iowa/18984/2013.

SEQ ID NO: 12 is the deduced amino acid sequence of the S protein encoded by SEQ ID NO: 3 North American PEDV strain North Carolina USA/NC/2013/35140.

SEQ ID NO: 13 is the deduced amino acid sequence of the S protein encoded by SEQ ID NO: 4 North American PEDV strain USA/Indiana12.83/2013.

SEQ ID NO: 14 is the deduced amino acid sequence of the S protein encoded by SEQ ID NO: 5 North American PEDV strain USA/Iowa/2013.

SEQ ID NO: 15 is the deduced amino acid sequence of the S protein encoded by SEQ ID NO: 6 North American PEDV strain 1251-125-10.

SEQ ID NO: 16 is the deduced amino acid sequence of the S protein encoded by SEQ ID NO: 7 Korean PEDV strain SM98.

SEQ ID NO: 17 is the deduced amino acid sequence of the S protein encoded by SEQ ID NO: 8 Korean attenuated PEDV strain KR-DR13-att.

SEQ ID NO: 18 is the nucleotide sequence of Korean PDCoV strain KOR/KNU14-04/2014 (GenBank Accession No. KM820765).

SEQ ID NO: 19 is the nucleotide sequence of North American PDCoV strain USA/Iowa459/2014 (GenBank Accession No. KR265865).

SEQ ID NO: 20 is the nucleotide sequence of North American PDCoV strain USA/Illinois121/2014 (GenBank Accession No. KJ481931).

SEQ ID NO: 21 is the nucleotide sequence of North American PDCoV strain USA/Minnesota454/2014 (GenBank Accession No. KR265854).

SEQ ID NO: 22 is the nucleotide sequence of North American PDCoV strain USA/Minnesota455/2014 (GenBank Accession No. KR265855).

SEQ ID NO: 23 is the nucleotide sequence of North American PDCoV strain USA/Arkansas61/2015 (GenBank Accession No. KR150443).

SEQ ID NO: 24 is the nucleotide sequence of North American PDCoV strain USA/Minnesota/2013 (GenBank Accession No. KR265853).

SEQ ID NO: 25 is the nucleotide sequence of North American PDCoV strain 8734/USA-IA/2014 (GenBank Accession No. KJ567050).

SEQ ID NO: 26 is the nucleotide sequence of North American PDCoV strain USA/NorthCarolina452/2014 (GenBank Accession No. KR265858).

SEQ ID NO: 27 is the nucleotide sequence of North American PDCoV strain HKU15 MI6148 (GenBank Accession No. KJ620016).

SEQ ID NO: 28 is the nucleotide sequence of North American PDCoV strain HKU15 OH11846 (GenBank Accession No. KT381613).

SEQ ID NO: 29 is the nucleotide sequence of North American PDCoV strain USA/Illinois272/2014 (GenBank Accession No. KR265856).

SEQ ID NO: 30 is the nucleotide sequence of North American PDCoV strain USA/Illinois273/2014 (GenBank Accession No. KR265857).

SEQ ID NO: 31 is the nucleotide sequence of North American PDCoV strain HKU15 IL2768 (GenBank Accession No. KJ584355).

SEQ ID NO: 32 is the nucleotide sequence of North American PDCoV strain USA/Nebraska209/2014 (GenBank Accession No. KR265860).

SEQ ID NO: 33 is the nucleotide sequence of North American PDCoV strain USA/Nebraska210/2014 (GenBank Accession No. KR265861).

SEQ ID NO: 34 is the nucleotide sequence of North American PDCoV strain HKU15 NE3579 (GenBank Accession No. KJ584359).

SEQ ID NO: 35 is the nucleotide sequence of North American PDCoV strain USA/Illinois449/2014 (GenBank Accession No. KR265852).

SEQ ID NO: 36 is the nucleotide sequence of North American PDCoV strain USA/Minnesota159/2014 (GenBank Accession No. KR265859).

SEQ ID NO: 37 is the nucleotide sequence of North American PDCoV strain USA/Michigan447/2014 (GenBank Accession No. KR265849).

SEQ ID NO: 38 is the nucleotide sequence of North American PDCoV strain USA/Michigan448/2014 (GenBank Accession No. KR265850).

SEQ ID NO: 39 is the nucleotide sequence of North American PDCoV strain PDCoV/USA/Iowa136/2015 (GenBank Accession No. KX022602).

SEQ ID NO: 40 is the nucleotide sequence of North American PDCoV strain PDCoV/USA/Nebraska145/2015 (GenBank Accession No. KX022605).

SEQ ID NO: 41 is the nucleotide sequence of North American PDCoV strain PDCoV/USA/Nebraska137/2015 (GenBank Accession No. KX022604).

SEQ ID NO: 42 is the nucleotide sequence of North American PDCoV strain PDCoV/USA/Minnesota140/2015 (GenBank Accession No. KX022603).

SEQ ID NO: 43 is the nucleotide sequence of North American PDCoV strain HKU15 PA3148 (GenBank Accession No. KJ584358).

SEQ ID NO: 44 is the nucleotide sequence of North American PDCoV strain USA/Indiana453/2014 (GenBank Accession No. KR265851).

SEQ ID NO: 45 is the nucleotide sequence of North American PDCoV strain USA/Minnesota292/2014 (GenBank Accession No. KR265864).

SEQ ID NO: 46 is the nucleotide sequence of North American PDCoV strain USA/Minnesota214/2014 (GenBank Accession No. KR265848).

SEQ ID NO: 47 is the nucleotide sequence of North American PDCoV strain USA/Minnesota442/2014 (GenBank Accession No. KR265847).

SEQ ID NO: 48 is the nucleotide sequence of North American PDCoV strain HKU15 SD3424 (GenBank Accession No. KJ584356).

SEQ ID NO: 49 is the nucleotide sequence of North American PDCoV strain USA/Ohio444/2014 (GenBank Accession No. KR265862).

SEQ ID NO: 50 is the nucleotide sequence of North American PDCoV strain USA/Ohio445/2014 (GenBank Accession No. KR265863).

SEQ ID NO: 51 is the nucleotide sequence of North American PDCoV strain HKU15 KY4813 (GenBank Accession No. KJ584357).

SEQ ID NO: 52 is the nucleotide sequence of Chinese PDCoV isolate PDCoV/CHJXNI2/2015 GenBank Accession No. KR131621).

SEQ ID NO: 53 is the nucleotide sequence of Chinese PDCoV strain CH/SXD1/2015 (GenBank Accession No. KT021234).

SEQ ID NO: 54 is the nucleotide sequence of Chinese PDCoV isolate CHN-JS-2014 (GenBank Accession No. KP757892).

SEQ ID NO: 55 is the nucleotide sequence of Chinese PDCoV isolate CHN-HB-2014 (GenBank Accession No. KP757891).

SEQ ID NO: 56 is the nucleotide sequence of Chinese PDCoV isolate CHN-HN-2014 (GenBank Accession No. KT336560).

SEQ ID NO: 57 is the nucleotide sequence of Chinese PDCoV strain NH (GenBank Accession No. KU981059).

SEQ ID NO: 58 is the nucleotide sequence of Chinese PDCoV strain NH isolate passage 0 (GenBank Accession No. KU981060).

SEQ ID NO: 59 is the nucleotide sequence of Chinese PDCoV strain CH/Sichuan/S27/2012 (GenBank Accession No. KT266822).

SEQ ID NO: 60 is the nucleotide sequence of Chinese PDCoV isolate CHN-AH-2004 (GenBank Accession No. KP757890).

SEQ ID NO: 61 is the nucleotide sequence of Thailand PDCoV strain PDCoV/Swine/Thailand/S5011/2015 (GenBank Accession No. KU051641).

SEQ ID NO: 62 is the nucleotide sequence of Thailand PDCoV strain PDCoV/Swine/Thailand/S5015L/2015 (GenBank Accession No. KU051649).

SEQ ID NO: 63 is the nucleotide sequence of Thailand PDCoV isolate TT_1115 (GenBank Accession No. KU984334).

DETAILED DESCRIPTION

I. Definitions

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

The terms "administer," "administering," "administration," and the like, as used herein, refer to methods that may be used to enable delivery of compositions to the desired site of biological action. These methods include, but are not limited to, intravenous, intramuscular, intradermal, intraperitoneal, subcutaneous, intravaginally, orally, topically, intrathecally, inhalationally, intranasally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa., which are incorporated herein by reference.

Certain methods of administration deliver the immunogenic composition to mucosal membranes. These include, but are not limited to, intranasal, oral, intravaginal, and rectal. In some embodiments, an adjuvant is selected to facilitate administration to mucosal membranes, and/or stimulate a mucosal immune response. The adjuvant may adhere to the mucosal membrane. Mucosal immune responses typically comprise the production of IgA antibodies but may also stimulate IgG responses, which may be advantageous in certain disclosed embodiments.

Intranasal formulations may include vehicles that neither cause irritation to the nasal mucosa nor significantly disturb ciliary function. Non-adjuvant diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Oral liquid preparations may be in the form of, for example, aqueous or oily suspension, solutions, emulsions, syrups or elixirs, or may be presented dry in tablet form or a product for reconstitution with water or other suitable vehicle before use. Such liquid preparations may contain conventional additives such as suspending agents, emulsifying agents, non-aqueous vehicles (which may include edible oils), or preservative.

As used herein, the terms "co-administration," "administered in combination with," and their grammatical equivalents, are meant to encompass administration of two or more therapeutic agents to a single subject, and are intended to include treatment regimens in which the agents are administered by the same or different routes of administration or at the same or different times. In some embodiments the one or more compositions described herein will be co-administered with other agents, including, but not limited to, therapeutics such as other vaccines, antibiotics, or combinations thereof. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compositions described herein and the other agent(s) are administered in a single composition. In some embodiments, the compositions described herein and the other agent(s) are admixed in the composition.

The term "effective amount" or "therapeutically effective amount" refers to the amount of an active agent (such as one or more compounds provided herein alone, in combination, or potentially in combination with other therapeutic agent(s)) sufficient to induce a desired biological result. That result may be amelioration or alleviation of the signs, symptoms, or causes of a disease, or any other desired alteration of a biological system. The term "therapeutically effective amount" is used herein to denote any amount of a therapeutic and/or preventative that causes an improvement in a disease condition. The amount can vary with the condition being treated, the stage of advancement of the condition, and the type and concentration of formulation applied. Appropriate amounts in any given instance will be readily apparent to those of ordinary skill in the art or capable of determination by routine experimentation such as vaccination and observation of an antibody response or vaccination followed by a challenge wherein the vaccinated animals perform better than non-vaccinated animals that are challenged similarly.

The compositions provided herein, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

The disclosed compositions can be formulated for parenteral administration, such as, for example, by intravenous, intraarterial, intramuscular, intradermal, intraperitoneal, and subcutaneous routes. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared. Suitable materials for such administration include sterile water; saline solution; glucose solution; aqueous vehicles, such as sodium chloride Injection, Ringer's Injection, Dextrose Injection, Dextrose, Sodium Chloride Injection, Lactated Ringer's Injection; ethyl alcohol, polyethylene glycol, and propylene glycol; non-aqueous vehicles such as, but not limited to, corn oil, cottonseed oil, peanut oil, sesame oil, ethyl oleate, isopropyl myristate, and benzyl benzoate; aqueous and non-aqueous, isotonic sterile injection solutions, which can contain antioxidants, buffers, bacteriostats, and solutes that render the formulation isotonic with the blood of the intended recipient; and aqueous and non-aqueous sterile suspensions that can include suspending agents, solubilizers, thickening agents, stabilizers, and preservatives. In the practice of this disclosure, compositions can be administered, for example, by intravenous infusion, orally, topically, intraperitoneally, intravesically or intrathecally. In an independent embodiment, parenteral administration, oral administration, and/or intravenous administration are the methods of administration. The formulations of compounds can be presented in unit-dose or multi-dose sealed containers, such as ampules, bottles, and vials.

"Coronavirus protein," such as PEDV or PDCoV protein, as used herein in reference to disclosed embodiments refers to any polypeptide product encoded by the coronavirus genome and/or produced only as a result of coronavirus infection or the coronavirus lifecycle. As used herein, a "polypeptide" has a length of from 2 amino acids to a length of a protein encoded by the coronavirus or a cell infected by a coronavirus, such as from 6 amino acids to a length of a protein, and/or a length sufficient to produce an antigenic response in a subject administered the polypeptide. Thus coronavirus specific polypeptides not encoded by a host cell but expressed by a coronavirus infected cell are within the scope of the term. Endogenous polypeptides encoded by a coronavirus infected cell, but expressed in the absence of coronavirus infection and/or lifecycle, are not intended. However, endogenous polypeptides expressed only as a consequence of coronavirus infection and/or lifecycle are within the scope of the term. The term also includes alternative forms of the polypeptides due to changes in secondary and/or tertiary structure, such as those resulting from partial or substantial protein denaturation as a non-limiting example. Thus denatured forms of the polypeptides are within the scope of the term.

PEDV protein refers to any polypeptide product encoded by the PEDV genome and/or produced as only as a result of PEDV infection or the PEDV lifecycle. Thus PEDV specific polypeptides not encoded by or expressed by a PEDV infected cell are within the scope of the term. Endogenous polypeptides encoded by a PEDV infected cell, but not expressed in the absence of PEDV infection and/or lifecycle, are not intended. However, endogenous polypeptides expressed only as a consequence of PEDV infection and/or lifecycle are within the scope of the term. The term also includes alternative forms of the polypeptides due to changes in secondary and/or tertiary structure, such as those resulting from partial or substantial protein denaturation as a non-limiting example. Thus denatured forms of the polypeptides are within the scope of the term.

The term "antigen" refers to a compound, composition, or substance that can stimulate the production of antibodies or a T-cell response in an animal, including compositions that are injected or absorbed into an animal. An antigen reacts with the products of specific humoral or cellular immunity. For example, PEDV antigen refers to any portion or fragment of a PEDV polypeptide that is recognized by an anti-PEDV antibody. In some cases, the portion or fragment may be a peptide with an attached moiety, such as, but not limited to, a sugar moiety, a phosphate moiety, or a lipid moiety. Alternatively, the portion or fragment may be a peptide without any attached non-peptide moieties.

Coronavirus antigen, such as a PEDV or PDCoV antigen, refers to any portion or fragment of a coronavirus polypeptide that is recognized by an anti-coronavirus antibody. In some cases, the portion or fragment may be a peptide with an attached moiety, such as, but not limited to, a sugar moiety, a phosphate moiety, or a lipid moiety. Alternatively, the portion or fragment may be a peptide without any attached non-peptide moieties.

The term "excipient," as used in this disclosure, is an additive that is used in combination with the coronavirus antigens. An excipient can be used, for example, to dilute an active agent, such as the coronavirus antigens, and/or to modify properties of a pharmaceutical composition. Examples of excipients include, but are not limited to, water, magnesium stearate, stearic acid, vegetable stearin, sucrose, lactose, starches, hydroxypropyl cellulose, hydoxypropyl methylcellulose, xylitol, sorbitol, maltitol, gelatin, polyethyleneglycol (PEG), phosphate buffered saline (PBS), carboxy methyl cellulose, vitamin A, vitamin E, vitamin C, retinyl palmitate, selenium, cysteine, methionine, citric acid, methyl paraben, propyl paraben, sugar, silica, talc, magnesium carbonate, sodium starch glycolate, tartrazine, aspartame, benzalkonium chloride, sesame oil, propyl gallate, sodium metabisulphite, lanolin, polyvinylpyrrolidone (PVP), tocopheryl polyethylene glycol 1000 succinate (also known as vitamin E TPGS, or TPGS), dipalmitoyl phosphatidyl choline (DPPC), trehalose, sodium bicarbonate, glycine, sodium citrate, lactose, saline, phosphate buffered saline or organic buffers including but not limited to Tris (hydroxymethyl)aminomethane, and metal chelating agents. Metal chelating agents include, but are not limited to, organic compounds such as the amino acids glutamic acid and histidine, organic diacids such as malate, and polypeptides such as phytochelatin, biomolecules such as pyochelin, pyoverdine, enterobactin and Dopa, and synthetic chelates such as ethylenediaminetetraacetic acid (EDTA).

An adjuvant refers to an agent that modifies the effect of another agent. As used herein, an adjuvant may be added to an immunogenic composition, such as a vaccine, to facilitate a beneficial result obtained by administering the immunogenic composition, such as by modifying the immune response to increase the amount of antibodies produced and/or increasing the length of protection conferred by the vaccine. An adjuvant may also be added to a composition to help stabilize a formulation of proteins and/or antigens in a vaccine composition. In some embodiments, the adjuvant is a non-naturally occurring chemical. Typically water by itself is not an adjuvant. Examples of adjuvants include, but are not limited to, inorganic compounds, such as alum, aluminum hydroxide, aluminum phosphate, aluminum sulfate, or calcium phosphate hydroxide; mineral oil, such as paraffin oil; organic esters such as aryl or aliphatic esters, particularly alkyl esters such as linear alkyl esters having up to at least 25 carbons, preferably up to 10 carbons; esters of acids or of alcohols containing a linear alkyl group, such as plant oils, ethyl oleate, propylene glycol di-(caprylate/caprate), glyceryl tri-(caprylate/caprate) or propylene glycol dioleate; esters of branched fatty acids or alcohols, in particular isostearic acid esters; oil-in-water emulsions, such as MF59 (U.S. Pat. No. 6,299,884) (containing 5% Squalene, 0.5% Tween 80, and 0.5% Span 85, optionally containing various amounts of MTP-PE) formulated into submicron particles using a microfluidizer such as Model 110Y microfluidizer (Microfluidics, Newton, Mass.)), and SAF (containing 10% Squalene, 0.4% Tween 80, 5% pluronic-blocked polymer LI 21, and threonyl-MDP, either microfluidized into a submicron emulsion or vortexed to generate a larger particle size emulsion), EMULSIGEW-based adjuvants including EMULSIGEN®, EMULSIGEN®-D (containing dimethyldioctadecylammonium bromide (DDA)), EMULSIGEN®-BCL (containing a block copolymer immunostimulant) and EMULSIGEN®-P (containing with a proprietary immunostimulant), and EMULSIGEN®-75 (a double adjuvant comprising an oil-in-water adjuvant with a cross-linked polymer) (Phibro Animal Health Corporation, Omaha, Nebr., USA); saponins, such as Stimulon™ QS-21 (Antigenics, Framingham, Mass.), described in U.S. Pat. No. 5,057,540, ISCOMATRIX (CSL Limited, Parkville, Australia), described in U.S. Pat. No. 5,254,339, and immunostimulating complexes (ISCOMS); surfactants, e.g., hexadecyl amine, octadecylamine, lysolecithin, dimethyldioctadecylammonium bromide, N,N-dioctadecyl-N'-N-bis(2-hydroxyethyl-propane di-amine), methoxyhexadecyl-glycerol, and pluronic polyols; copolymers, including low molecular weight copolymers such as Polygen™ (available from Phibro Animal Health Corporation, Omaha, Nebr., USA); polanions, e.g., pyran, dextran sulfate, and poly IC; peptides, e.g., muramyl dipeptide, MPL, aimethylglycine, tuftsin, oil emulsions, alum, and mixtures thereof.

Unsaturated carboxylic acid polymers also may be useful as adjuvants for the disclosed compositions. Such polymers include polymers of acrylic or methacrylic acid, copolymers of maleic anhydride and alkenyl derivative and cross-linked acrylic acid polymers, such as polyacrylate or polyacrylic acid polymers, optionally cross-linked with polyalkenyl ethers of sugars or polyalcohols (carbomers). In certain embodiments, polymers comprising moieties having from 2 to 10 carbon atoms, more particularly 2 to 4 carbon atoms are preferred, e.g. vinyls, allyls and other ethylenically unsaturated groups. The unsaturated radicals may be optionally substituted, such as with one or more alkyl moieties including methyl. Such polymers include polymers are sold under the name carbopol (cross-linked with an allyl sucrose or with allyl pentaerythritol) including carbopol 934P, carbopol 971P and carbopol 974P (available from Lubrizol Corporation, Wickliffe, Ohio)) and the polymer sold under the name CARBIGEN™ (available from Phibro Animal Health Corporation, Omaha, Nebr., USA). Copolymers of maleic anhydride and alkenyl derivative include the copolymers EMA (Monsanto) that are copolymers of maleic anhydride and ethylene. In certain embodiments, an adjuvant comprising an unsaturated carboxylic acid polymer, such as an adjuvant comprising carbopol, or CARBIGEN™, are advantageous for administration to mucus membranes, such as via intranasal, oral, vaginal and rectal routes.

Other exemplary adjuvants include bacterial lipopolysaccharides; synthetic polynucleotides such as oligonucleotides containing a CpG motif (e.g., U.S. Pat. No. 6,207,646); IC-31 (Intercell AG, Vienna, Austria), described in European Patent Nos. 1 296 713 and 1 326 634; a pertussis toxin (PT) or mutant thereof, a cholera toxin or mutant thereof (e.g., U.S. Pat. Nos. 7,285,281, 7,332,174, 7,361,355 and 7,384,640); or an E. coli heat-labile toxin (LT) or mutant thereof, particularly LT-K63, LT-R72 (e.g., U.S. Pat. Nos. 6,149,919, 7,115,730 and 7,291,588); bacterial products, such as killed bacteria Bordetella pertussis, Mycobacterium bovis, or toxoids; B peptide subunits of E. coli heat labile toxin or cholera toxin (McGhee, J. R., et al., "On vaccine development," Sem. Hematol., 30:3-15 (1993)); nonbacterial organics, such as squalene or thimerosal; delivery systems, such as detergents (Quil A); cytokines and/or lymphokines, such as interleukins 1-a, 143, 2, 4, 5, 6, 7, 8 and 10, 12 (see, e.g., U.S. Pat. No. 5,723,127), 13, 14, 15, 16, 17 and 18 (and its mutant forms); the interferons-a, β and γ; granulocyte-macrophage colony stimulating factor (GM-CSF) (see, e.g., U.S. Pat. No. 5,078,996 and ATCC Accession Number 39900); macrophage colony stimulating factor (M-CSF); granulocyte colony stimulating factor (G-CSF); and the tumor necrosis factors a and β; chemokines, such as MCP-1, MIP-Iα, MIP-Iβ, and RANTES; adhesion molecules, such as a selectin, e.g., L-selectin, P-selectin and E-selectin; mucin-like molecules, such as CD34, GlyCAM-1 and MadCAM-1; a member of the integrin family, such as LFA-1, VLA-1, Mac-1 and p150.95; co-stimulatory molecules, such as CD40 and CD40L; immunoglobulin superfamily members, such as PECAM, ICAMs, e.g., ICAM-1, ICAM-2 and ICAM-3, CD2 and LFA-3; growth factors including vascular growth factor, nerve growth factor, fibroblast growth factor, epidermal growth factor, B7.2, PDGF, BL-1, and vascular endothelial growth factor; receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6; Caspase (ICE); muramyl peptides, such as N-acetyl-muramyl-L-threonyl-D-isoglutamine (thr-MDP), N-acetyl-normuramyl-L-alanine-2-(1 '-2' dipalmitoyl-sn-glycero-3-hydroxyphosphoryloxy)-ethylamine (MTP-PE); the B peptide subunits of E. coli heat labile toxin or of the cholera toxin; the RIBI adjuvant system (Ribi Inc.); pluronic polyols; Amphigen; Avridine; L121/squalene; D-lactide-polylactide/glycoside; MPL™ (3-O-deacylated monophosphoryl lipid A, Corixa, Hamilton, Mont.; described in U.S. Pat. No. 4,912,094); synthetic lipid A analogs; aminoalkyl glucosamine phosphate compounds (AGP), or derivatives or analogs thereof (Corixa, Hamilton, Mont.; described in U.S. Pat. No. 6,113,918), including 2-[(R)-3-tetradecanoyloxytetradecanoylamino]ethyl 2-deoxy-4-O-phosphono-3-O—[(R)-3-tetradecanoyoxytetradecanoyl]-2-[(R)-3-tetradecanoyloxytetradecanoylamino]-β-D-glucopyranoside (529, RC529, optionally formulated as an aqueous form (AF) or as a stable emulsion (SE)); and combinations, such as Freund's complete adjuvant or Freund's incomplete adjuvant. Alternatively, or additionally, the proteins and antigens may be the incorporated into liposomes for use in an immunogenic composition, such as a vaccine, or may be conjugated to proteins, such as keyhole limpet hemocyanin (KLH) or human serum albumin (HSA) and/or other polymers.

The term "pharmaceutically acceptable carrier" refers to an excipient that is a carrier or vehicle, such as a suspension aid, solubilizing aid, or aerosolization aid. *Remington: The Science and Practice of Pharmacy*, The University of the Sciences in Philadelphia, Editor, Lippincott, Williams, & Wilkins, Philadelphia, Pa., 21$^{st}$ Edition (2005), incorporated herein by reference, describes additional compositions and formulations suitable for pharmaceutical delivery of one or more therapeutic compositions and/or pharmaceutical agents.

In general, the nature of the carrier will depend on the particular mode of administration being employed. For instance, parenteral formulations usually comprise injectable fluids that include pharmaceutically and physiologically acceptable fluids, such as water, physiological saline, balanced salt solutions, aqueous dextrose, glycerol, or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The term "immune response" refers to a response of a cell of the immune system, such as a B-cell, T-cell, macrophage or polymorphonucleocyte, to a stimulus such as an antigen. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection).

The terms "isolated proteins and antigens" and "isolated coronavirus proteins and antigens," as used herein, refers to proteins and antigens separated from the culture medium or supernatant. The isolated proteins and antigens typically comprise cell material, such as cell wall fragments, and proteins and antigens released from the infected cells, such as by a detergent or freeze-thawing. The isolated proteins and antigens may be in a buffer solution.

The term "substantial identity" in the context of a peptide indicates that a peptide comprises a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%, sequence identity to a reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

The term "vaccine" refers to a preparation of immunogenic material capable of stimulating an immune response, administered for the prevention, amelioration, or treatment of disease, such as an infectious disease. The immunogenic material may include, for example, antigenic proteins, peptides or DNA derived from them. Vaccines may elicit prophylactic (preventative) and/or therapeutic responses. Methods of administration vary according to the vaccine, but may include inoculation, ingestion, inhalation or other forms of administration as discussed herein. Inoculations can be delivered by any of a number of routes, including parenteral, such as intravenous, subcutaneous, intramuscular, intranasal, oral, vaginal or rectal. Vaccines may be administered with an adjuvant to boost the immune response.

II. Overview

Coronaviruses are enveloped viruses and have a positive-sense single-stranded RNA genome. The coronavirus genome is typically from about 25 to 32 kilobases. Substantially all coronaviruses have spike (S) proteins, envelope, membrane, and nucleocapsid proteins that contribute to the overall viral structure.

With respect to porcine coronaviruses, PEDV is a member of the subfamily Coronavirinae of the genus Alphacoronavirus. It is an enveloped virus possessing approximately a 28 kb, positive-sense, single stranded RNA genome. Although first identified in 1971 in England, variant strains of PEDV emerging since 2010 in China, and since 2013 in North America, have been associated with large-scale outbreaks of diarrhea have been more acute and severe than those associated with the early European outbreaks. These recent Chinese and North American strains have been identified as belonging to Genogroup 2. Typically, the homology between strains in this genotype is very similar. For example, North American strains typically have about 99% homology. However, the North American strains and recent China strains have less similarity to strains from Europe and Asia that are Genogroup 1. For example, FIG. 9 shows a comparison of the homologies of seven Genogroup 2 strains from North America (SEQ ID NOS: 1-6) and China in 2012 (SEQ ID NO: 9). DR13, an attenuated Korean strain of Genogroup 1 (SEQ ID NO: 8), the sequence of which would be known to a person of ordinary skill in the art based on the disclosure provided by WO 2015/120378, incorporated herein by reference, as the sequence was known; and SM98, a Korean strain of Genogroup 1 (SEQ ID NO: 7). SM98 has 96.6 to 96.9% homology with the Genogroup 2 strains, but the Genogroup 2 strains are at least 99%, such as 99.1-99.9%, homologous with each other.

Figure 10A:
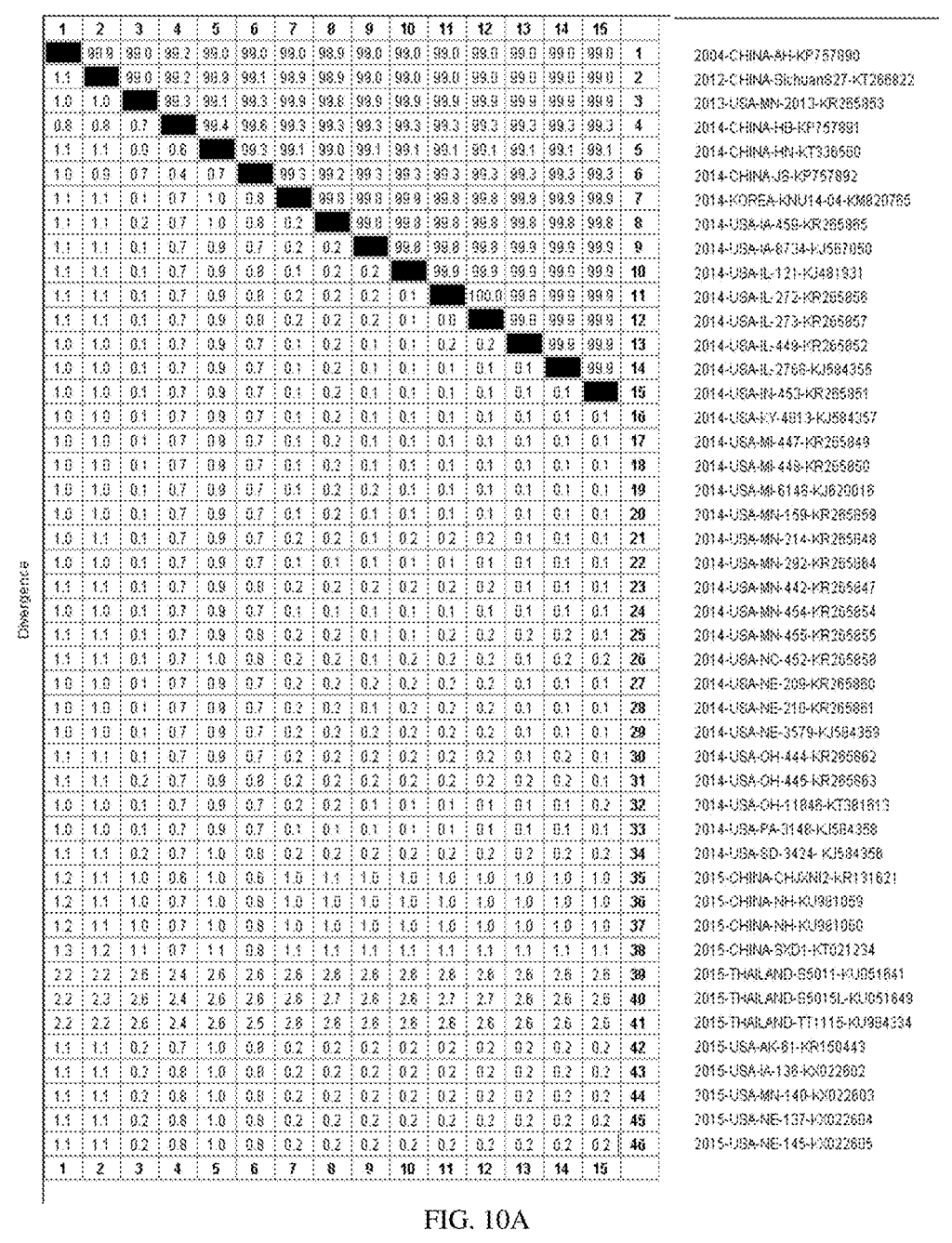
Figure 10B:
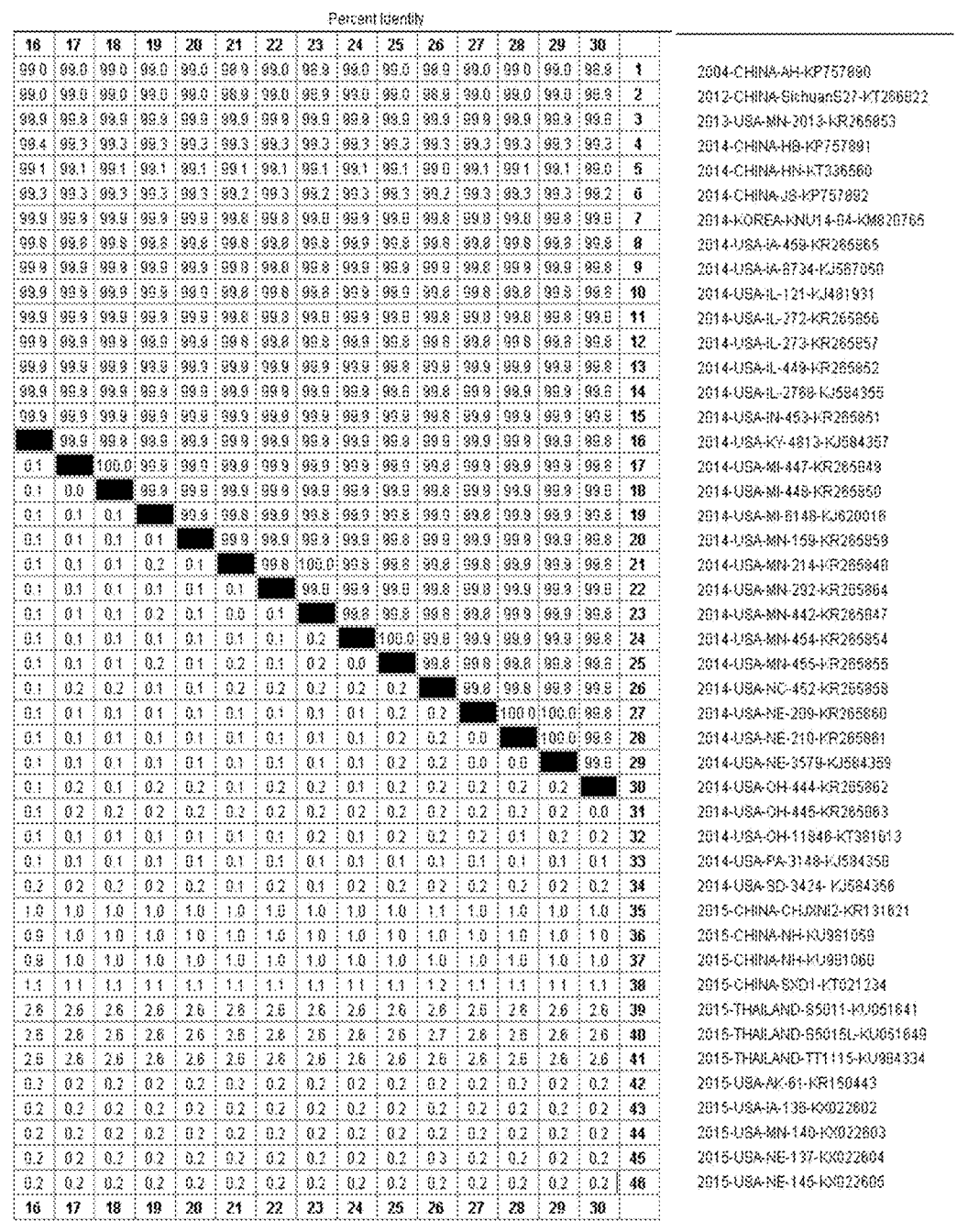
Figure 10C:
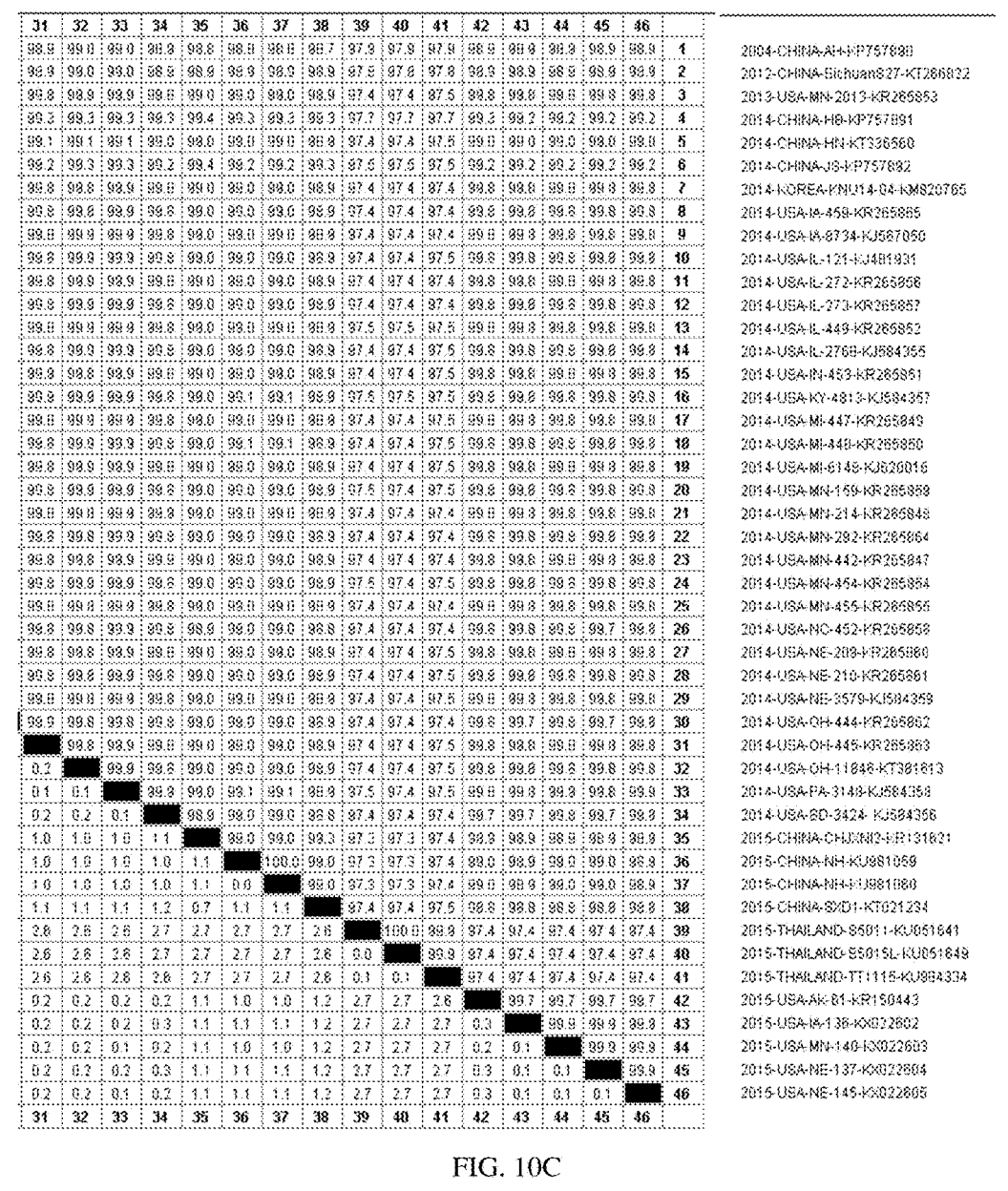
Figure 11:
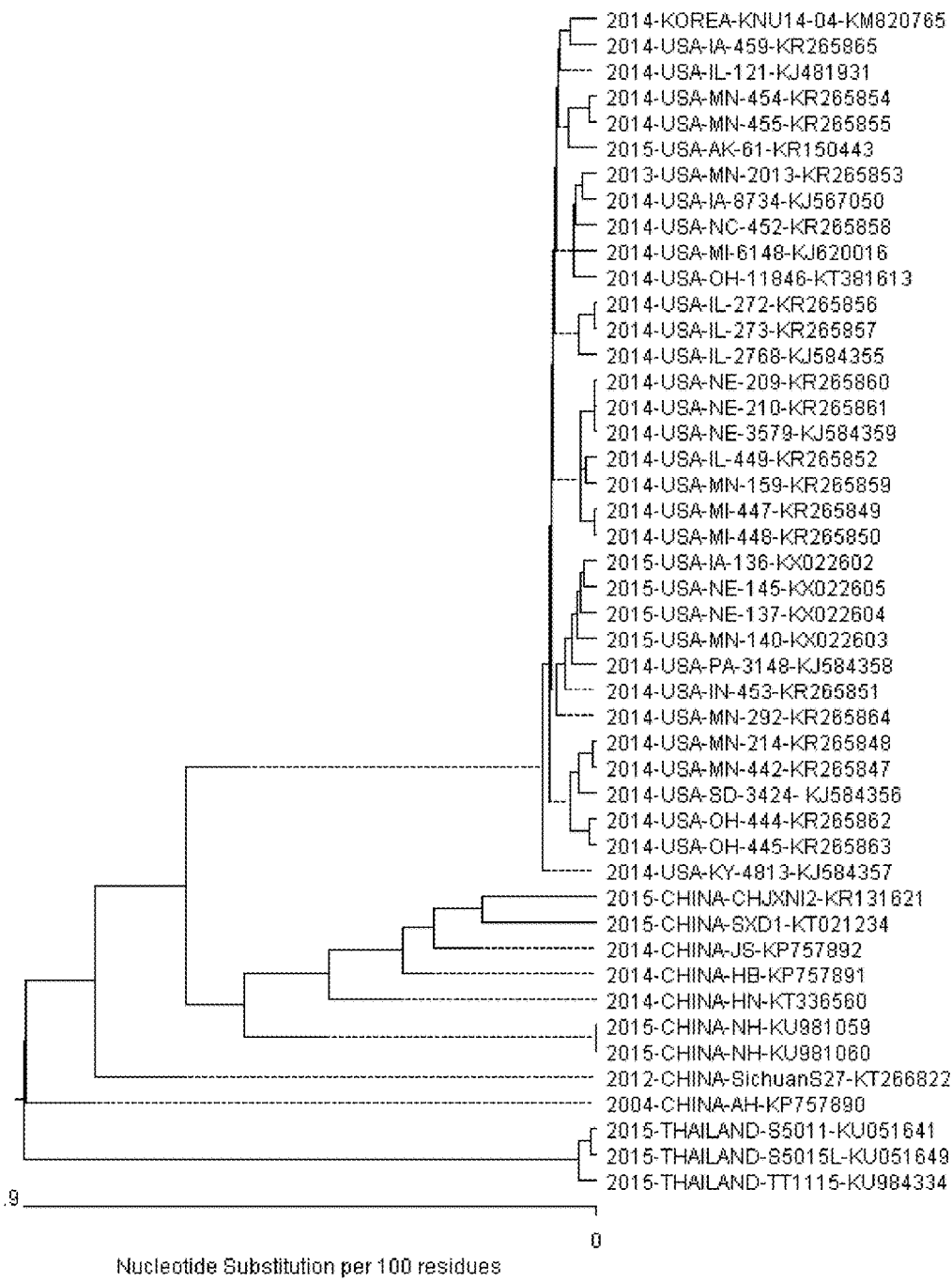
FIG. 11 is a schematic diagram illustrating the relationship between the PDCoV strains or isolates of SEQ ID NOS: 18-63 in terms of nucleotide substitutions per 100 residues.

Porcine deltacoronavirus (PDCoV) was identified in several states across the United Sates in 2014. Symptoms of PDCoV infection include watery diarrhea, vomiting and dehydration. The genomic sequence of PDCoV is about 25-26 kilobases, excluding the 3' poly(A) tail. Typically, PDCoV strains in the U.S. have at least 99% homology with each other, such as at least 99.2%, at least 99.4%, or at least 99.5% homology with other U.S. strains. U.S. strains also have at least 85% homology with Chinese, Korean, and/or Thai strains or isolates, such as at least 90%, at least 95%, or at least 97% homology. FIGS. 10A-10C shows a comparison of the homologies of 46 strains or isolates from Korea (SEQ ID NO: 18), North America (SEQ ID NOS: 19-51), China (SEQ ID NOS: 52-60) and Thailand (SEQ ID NOS: 61-63). And FIG. 11 shows the relationship between the strains or isolates of SEQ ID NOS: 18-63 in terms of nucleotide substitutions per 100 residues.

Disclosed herein are embodiments of a method for making a coronavirus immunogenic composition, such as a PEDV or PDCoV immunogenic composition, comprising incubating coronavirus infected cells for an effective period of time to result in one or more replicated coronavirus viral particles being released, such as from 24 to 60 hours or from 24 to 48 hours, isolating cells infected with coronavirus away from cell-free coronavirus virus particles to form cells containing cell-associated coronavirus proteins and antigens, separating the coronavirus proteins and antigens from the isolated cells to form a first solution comprising isolated coronavirus proteins and antigens, and optionally inactivating viral particles in the first solution to produce a second solution. Any embodiments of the method may further comprise adding an adjuvant to the second solution. The adjuvant may be any adjuvant suitable for use with the coronavirus proteins and antigens. The adjuvant may be selected to stimulate a mucosal antibody response and/or may be selected for intranasal administration and/or intravaginal administration. The adjuvant may adhere to the mucous membranes, and/or comprise polyacrylic acid. In any of the disclosed embodiments, the immunogenic composition may be a vaccine and/or may be formulated for intranasal administration. Any embodiments of the method may comprise extracting coronavirus proteins and antigens, eluting coronavirus proteins and antigens, a freeze-thaw cycle, or a combination thereof. In particular embodiments, the coronavirus is PEDV, or PDCoV.

Also disclosed are embodiments of an immunogenic composition comprising a first antigenic component comprising isolated coronavirus proteins and/or antigens from a first coronavirus strain. The immunogenic composition may comprise an amount of S protein, such as an amount sufficient to produce an immune response in a subject receiving the immunogenic composition. The S protein may be an intact S protein. In any of the above embodiments, the immunogenic composition may comprise a second antigenic component. The second antigenic component may comprise isolated coronavirus proteins and/or antigens from a second coronavirus species and/or strain or isolated proteins and/or antigens from a second pathogen other than a coronavirus. In some embodiments, second pathogen is porcine reproductive and respiratory syndrome virus, and in other embodiments, the second pathogen is *Mycoplasma hyopneumoniae*. However, in certain embodiments when the coronavirus is or comprises PEDV, the second pathogen is not *Mycoplasma hyopneumoniae*.

In any of the above embodiments, the immunogenic composition may be a vaccine and/or may comprise an adjuvant selected to stimulate an antibody response. The adjuvant may be selected to stimulate a mucosal antibody response and/or adhere to the mucous membranes. The adjuvant may comprise a polyacrylic acid adjuvant and/or an emulsified oil-in-water adjuvant. The adjuvant may comprise an ammonium salt, such as a tetraalkylammonium salt, and in certain embodiments, the adjuvant comprises dimethyldioctadecylammonium bromide.

Also disclosed are embodiments of a method of administering to a subject an effective amount of any embodiment of the immunogenic composition disclosed herein. In some embodiments, the subject is less than 7 days old, such as 5 days old or less, or 2 days old or less. In any of the above embodiments, administering may comprise administering orally, intramuscularly, or subcutaneously, or it may comprise administering intranasally. In particular embodiments, the subject is a swine.

In any of the above embodiments where the subject is a swine, the method may comprise administering a first immunogenic composition to a sow, and administering a second immunogenic composition to at least one piglet farrowed from the sow, the second immunogenic composition, and optionally the first immunogenic composition, independently being any embodiment of the immunogenic composition disclosed herein. In any embodiments, the second immunogenic composition may be administered intranasally and/or the first immunogenic composition may be administered intramuscularly.

In any of the above embodiments, the subject may be a pregnant sow, or a sow expected to become pregnant subsequent to administration of the first immunogenic composition. The first immunogenic composition may be administered at a time point prior to the sow becoming pregnant such that, when pregnant, the sow has a greater immunity to PEDV compared to a pig not administered the immunogenic composition.

Further disclosed are embodiments of a use of any embodiments of the immunogenic composition disclosed herein in the manufacture of a medicament for administration to a subject, such as a pig.

III. Method of Extracting or Eluting Coronavirus Proteins and/or Antigens

The disclosure is based in part on the availability and knowledge of cell culture techniques and their use in the propagation of viruses, such as coronaviruses including, but not limited to, PEDV and PDCoV. MJ Biologics, Inc., is also the assignee of U.S. Pat. Nos. 7,241,582, 7,449,296, 7,776, 537 and 8,142,788, all incorporated herein in their entirety by reference, which provide additional information relating to cell culture techniques and their use in the propagation of the porcine reproductive and respiratory syndrome virus (PRRSV). The disclosure may be practiced by use of any suitable cell line susceptible to coronavirus infection and intracellular replication in vitro. Thus the infected cell may be any that is capable of being productively infected by the coronavirus. Non-limiting examples include mammalian cell, such as porcine cells, either in vitro or in vivo. One non-limiting example of cells in vitro is primary cells from a porcine subject that is infected with a coronavirus, such as PEDV or PDCoV. Other non-limiting examples include simian cell lines, such as MA-104; VERO cells; BGM cells; MDCK cells and ST cells. In certain embodiments, MARC cells are used.

With respect to PEDV, the disclosure may be practiced by use of any suitable cell line susceptible to PEDV infection and intracellular replication in vitro, such as PEDV having at least a 90% sequence identity (i.e., 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100%) to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9. In certain embodiments, the PEDV has at least 90% sequence identity (i.e., 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100%) to SEQ ID NO: 1, SEQ ID NO: 2, SEQ ID NO: 3, SEQ ID NO: 4, SEQ ID NO: 5, or SEQ ID NO: 6. Thus the infected cell may be any that is capable of being productively infected by PEDV. Non-limiting examples include porcine cells, either in vitro or in vivo. One non-limiting example of cells in vitro is primary cells from a porcine subject that is infected with PEDV. Other non-limiting examples are with the use of a simian cell line, such as MA-104; VERO cells; BGM cells; MDCK cells; MARC cells, and ST cells.

With respect to PDCoV, the disclosure may be practiced by use of any suitable cell line susceptible to PDCoV infection and intracellular replication in vitro, such as PDCoV having at least a 90% sequence identity (i.e., 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100%) to one or more of SEQ ID NOS: 18-63. In certain embodiments, the PDCoV has at least 90% sequence identity (i.e., 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100%) to one or more of SEQ ID NOS: 19-51. Thus the infected cell may be any that is capable of being productively infected by PDCoV. Non-limiting examples include porcine cells, either in vitro or in vivo. One non-limiting example of cells in vitro is primary cells from a porcine subject that is infected with PDCoV. Other non-limiting examples are with the use of a simian cell line, such as MA-104; VERO cells; BGM cells; MDCK cells; MARC cells, and ST cells.

Infection of cells with the coronavirus, such as PEDV or PDCoV, may be at any suitable multiplicity of infection (m.o.i.), such as 0.1, 0.5 or 1, and infection of all cells in a culture is not required. In some cases, initial infection of some cells in a culture may be followed by subsequent release of infectious coronavirus that infects non-infected cells in the culture. The infected cells may still be used in the practice of the disclosed methods.

After contact and infection with the coronavirus, the virus is allowed to intracellularly reproduce its proteins and antigens, and so replicate, for a suitable period of time. The suitable period of time may vary between different coronaviruses, isolates, strains, and/or subtypes. In some embodiments, post-infection times range from 1 hour to at least 3 days, such as from 6 hours to 3 days, from 12 hours to 60 hours, or from 24 hours to 48 hours. Other post-infection times include about 12 hours, about 18 hours, about 24 hours, about 30 hours, about 36 hours, about 42 hours, about 48 hours, about 54 hours, about 60 hours, and about 66 hours. Coronavirus culture, such as PEDV or PDCoV culture, typically does not go for more than four days, and thus the harvest may be a late term harvest, such as after 24 hours. This is in contrast to PRRSV, where the proteins and antigens are typically harvested at an early term harvest at 28-60 hours post infection. A person of ordinary skill in the art will understand that 'early term' and 'late term' are virus dependent. For example a PRRSV culture will typically take 5 days to finish, whereas a coronavirus culture, such as PEDV or PDCoV culture, will typically finish after 3 days.

A method of assessing coronavirus protein production over time, after infection, also is disclosed to determine possible time points for isolation of infected cells and collection of viral proteins and/or antigens from the cells. In some embodiments, the method comprises taking samples at different time points after infecting the cells with the virus. The time points may be based on the percentage of cytopathic effect (CPE %), such as 15%, 20%, 25%, 30%, 35%, 40%, 50%, 60%, 70%, 80% and/or 90%. Sampling may comprise separating the supernatant from the cells, such as by pouring. The cells may be in a suitable culture vessel, such as a T25, T75 or roller bottle. After separation, an extraction buffer is added to the vessel containing the cells. Typically, the amount of buffer added is from about one half to about one tenth volume of the supernatant volume, such as from about one quarter to about one eighth, or from about one fifth to about one sixth volume of the supernatant volume. The vessel is agitated, such as by rocking and/or rolling. The agitation is performed for a time period and at a temperature sufficient to facilitate extraction of the proteins and antigens. The time period may be from greater than 0 to at least 60 minutes, such as from 1 minute to 30 minutes, or from 5 minutes to 20 minutes. The temperature may be any temperature suitable to facilitate the extraction, such as from greater than zero to at least 50° C., from 10° C. to 40° C., from 20° C. to 30° C., or about 25° C. The temperature may be an ambient temperature. The extraction buffer is then separated and the extracts analyzed by a suitable technique, such as Western blot, to provide data concerning the presence and/or amount of target antigen versus time. An optimal harvest time is selected based on the data. Typically, the optimal harvest time provides the culture time, or range of culture times, that provide a desired CPE % and/or desired target antigen content.

This "time course" assessment after infection may be used to select a post infection time point for the preparation of viral proteins and/or antigens. The assessment is optionally performed for each coronavirus isolate, strain, and/or subtype. The protein and/or antigen yields may also be compared using different coronavirus isolates and different days after virus inoculation, and optimal conditions for the highest antigenic yields may be determined by comparative testing.

Coronaviruses produces several proteins, including spike protein. With respect to PEDV, the spike protein has a molecular weight of about 152 kDa based on deduced amino acid sequences. After post-translational modifications the protein may have a molecular weight of from 180 kDa to at least 350 kDa, depending, for example, on the amount of post-translational glycosylation. The molecular weight may be determined by any suitable technique, such as, for example Western blot. PEDV spike protein has been predicted to comprise two portions—S1 at the N-terminus and S2 at the C-terminus. The spike protein may be a spike protein encoded by a PEDV having least 90% sequence identity (i.e., 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100%) to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9. In certain embodiments, the spike protein is encoded by a PEDV having least 90% identity (i.e., 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100%) to SEQ ID NO: 1, SEQ ID NO: 2, SEQ ID NO: 3, SEQ ID NO: 4, SEQ ID NO: 5, or SEQ ID NO: 6. The spike protein may have a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, sequence identity to SEQ ID NO: 10, SEQ ID NO: 11, SEQ ID NO: 12, SEQ ID NO: 13, SEQ ID NO: 14, SEQ ID NO: 15, SEQ ID NO: 16, or SEQ ID NO: 17. In certain embodiments, the spike protein may have a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, sequence identity to SEQ ID NO: 10, SEQ ID NO: 11, SEQ ID NO: 12, SEQ ID NO: 13, SEQ ID NO: 14, or SEQ ID NO: 15. An indication that two peptide sequences are substantially identical is that one peptide is immunologically reactive with antibodies raised against the second peptide. Thus, a peptide is substantially identical to a second peptide, for example, where the two peptides differ only by a conservative substitution.

Without being bound to a particular theory, the coronavirus proteins and antigens, such as PEDV and PDCoV proteins and antigens, produced by the disclosed method include spike proteins in multiple glycosylation states. This is due, in part, to breaking open the infected cells to separate and release the proteins and antigens substantially before viral particles are released into the culture medium. As a result, spike protein glycosylation is in progress, rather than being substantially completed, and therefore, the separated spike proteins have a range of molecular weights. By administering to a subject an immunogenic composition comprising such spike proteins, the subject is exposed to spike proteins having different glycosylation states, and thus produces antibodies to these proteins. This may be advantageous for the subject, compared to a subject that is administered either a composition that only includes non-glycosylated spike protein, such as a recombinant protein generally from prokaryote, or a composition that has substantially only fully glycosylated spike protein, such as a conventional killed vaccine that is typically made with fully grown virus culture material.

In some embodiments, post-infection times are selected to provide an amount of the spike protein in the composition, such as an extract or eluant, sufficient to provide an immune response, such as a protective immune response, in a subject.

In certain embodiments, the post-infection time is selected such that coronavirus viral particles are present in the culture medium prior to the collecting, extracting and/or eluting process. In some embodiments, the proteins and/or antigens, such as the spike protein, harvested from coronavirus infected cells, such as PEDV or PDCoV infected cells, may be in greater amounts than those available from coronavirus particles in the culture medium, such as at least 2×, 3×, 4×, 5× or more than 5× the amount available from coronavirus particles in the culture medium.

In some embodiments, the proteins and/or antigens harvested from coronavirus infected cells may be in greater amounts than those available from coronavirus particles in the culture medium. At some time points after infection, the majority, or entirety, of the replicated coronavirus proteins may remain associated with the infected cells or are otherwise part of a cell associated viral component (CAVC). Thus the majority or entirety of coronavirus proteins and/or antigens are either within the infected cells or associated with the cell membrane of the infected cells. Under such conditions, relatively few, if any, coronavirus particles are present in the extracellular environment. The preparation of CAVC from an early time point, such as before the production of coronavirus particles and/or the release thereof into the extracellular environment also has the benefit of increased safety in that few, if any, infectious viral particles are present as a contaminant. In some embodiments, no infectious viral particles are present as a contaminant.

However, in other embodiments, it was surprisingly found that harvesting the proteins and antigens at a time point after the infected cells had released replicated coronavirus viral particles, such as PEDv or PDCoV viral particles, resulted in improved results. This was in contrast to results obtained with certain other viruses, such as PRRSV, as disclosed in U.S. Pat. Nos. 7,241,582, 7,449,296, 7,776,537, and 8,142,788.

In some embodiments, the method of preparing coronavirus proteins and antigens from coronavirus infected cells comprises providing a population of cells infected with coronavirus; isolating the infected cells away from cell-free coronavirus to form cells containing cell-associated coronavirus proteins and antigens; and extracting or eluting coronavirus proteins and antigens from the isolated cells. In some disclosed embodiments, the coronavirus is PEDV. In other embodiments, the coronavirus is PDCoV. The composition may be a solution. The coronavirus may comprise one or more species and/or one or more strains of coronavirus, such as two or more species and/or strains having at least one nucleotide difference between their genomes.

As used herein, the terms "separating" and "separation" refer to, by way of unlimited examples, breaking open, extracting, eluting, rupturing, lysing, centrifuging, filtering, or a combination thereof, to release the proteins and antigens from within the isolated cells. The composition may also comprise cell fragments. In cases wherein there is no cell-free virus present, then isolating the infected cells away from cell-free coronavirus may comprise isolating the infected cells from other materials that may interfere with the method, such as the culture medium used with the cells. The isolation step may be performed by any means known in the art, such as by simply pouring off the medium and leaving the cells to be extracted by detergents or freeze/thaw, or use of centrifugation to generate a cell pellet and supernatant. The supernatant can then be removed and/or discarded, such as by use of a membrane filtration, to leave the cells. The separation of viral proteins and antigens may be performed by any suitable method, such as extraction, elution and/or freeze-thawing. The extraction step is optionally performed by re-suspending the cells in a buffer. In some embodiments, the isolation step may be performed by simply pouring off the medium and leaving the cells on culture devises such as flasks, roller bottles or cell culture carriers to be extracted by detergents or freeze/thawing with buffer. The extraction or elution is performed with a detergent-containing solution, thus the buffer used to re-suspend cells may contain detergent. In other embodiments, the extraction may be performed by freeze-thaw method. Optionally, the viral proteins and/or antigens produced by the method include coronavirus envelope proteins.

In some embodiments, the method comprises using a population of cells that has been infected with coronavirus for a sufficient time to produce little to undetectable amounts of infectious units per ml of supernatant, such as the culture media used with the cells. In some embodiments, the time is sufficient to produce tissue culture infective doses/ml ($TCID_{50}$/ml) of from $10^1$ to $10^{10}$, such as from $10^1$ to $10^7$, or from $10^1$ to $10^{5.5}$. Non-limiting examples include using less than $10^{5.5}$, such as $10^4$ or less, or $10^3$ or less $TCID_{50}$/ml.

The detergent-containing solution may be any that is suitable for extracting or eluting coronavirus proteins and/or antigens. One non-limiting example of a suitable class of detergents is non-ionic detergents. Particular exemplary detergents include, but are not limited to poly(ethylene glycol) p-isooctyl-phenyl ether, octylphenoxypolyethoxyethanol (Nonidet P-40), or 4-(1,1,3,3-tetramethylbutyl)phenyl-polyethylene glycol (Triton X-100). The detergent is used at a concentration effective for extracting or eluting coronavirus proteins and/or antigens, such as a concentration of from greater than zero to 5% in solution, such as from greater than zero to 2%, 0.25% to 1%, or 0.5% in solution. In certain embodiments, the detergent is a solution of 0.5% Triton X-100. The collecting, extracting and/or eluting may be for from greater than zero to at least about 24 hours, such as from 0.1 hours to 24 hours, 0.1 hours to 15 hours, 0.2 hours to 10 hours or 0.2 hours to 5 hours, or in certain embodiments from 2 hours to 15 hours. The collecting, extracting and/or, eluting is performed at a suitable temperature. In some embodiments, the temperature is from zero to less than 30° C., such as from 0° C. to 25° C., from 1° C. to 20° C., from 2° C. to 10° C. or from 2° C. to 6° C., and in certain embodiments is 4° C., or room temperature, such as from 20 to 25° C. Optionally, the viral proteins and/or antigens produced by the method include coronavirus envelope proteins.

For a freeze-thaw process a buffer may be added to the cells, typically after the culture medium is removed. The buffer can be any suitable buffer, such as Tris or phosphate buffered saline (PBS) with or without chelating agents, such as EDTA as non-limiting example. The cells are coated with the buffer, such as by agitation, for example, swirling or stirring. The cells are then placed in a freezer at a temperature suitable to freeze the cells and buffer, such as −10° C. or below. After the cells are frozen, they are allowed to thaw. The thawing causes cells to break, thereby releasing the proteins and antigens. Additional freeze-thaw cycles may be performed to release additional proteins and antigens.

After the release of the proteins and antigens, an inactivating agent may be added. Suitable inactivating agents include any agent that will inactivate viral particles present in the solution of viral protein and antigens, such as binary ethyleneimine (BEI), formalin, or beta propiolactone (BPL). The concentration of activating agent may be from 0.01 mol/L to at least 2 mol/L, such as from 0.01 mol/L to 1 mol/L. The solution of viral protein and antigens is mixed with the inactivating agent until inactivation is complete, such as for from 5 minutes to 48 hours or more, such as 15 minutes to 2 hours, or from 30 minutes to 1 hour. The inactivation process can be stopped by the addition of a sufficient amount of thiosulfate solution, such as sodium thiosulfate, to neutralize the excess inactivating agent. After inactivation, the solution of viral protein and antigens may be optionally diluted before a suitable adjuvant is added to the solution to produce the immunogenic composition.

The immunogenic composition will contain an effective amount of coronavirus antigens, such as PEDV or PDCoV antigens, in the solution, the effective amount being readily determined by a person of ordinary skill in the art. The effective amount may be sufficient to produce a desired immune response in a subject, such as a substantially protective immune response. The amount of coronavirus antigens may typically range from about 1% to about 95% (w/w) of the composition, or even higher or lower if appropriate. The quantity to be administered depends upon factors such as the age, weight and physical condition of the individual considered for vaccination. The quantity also depends upon the capacity of the subject's immune system to synthesize antibodies, and the degree of protection desired. Effective dosages can be readily established by a person of ordinary skill in the art through routine trials establishing dose response curves. In some embodiments, the concentration of viral antigens in the solution of coronavirus protein and antigens is from 0.01 ng/ml to 10,000 ng/ml, such as from 0.1 ng/ml to 5,000 ng/ml, from 0.5 ng/ml to 1,000 ng/ml or from 1 ng/ml to 100 ng/ml. The volume of the dosage is from greater than 0 mL to at least 10 mL, such as from 0.1 mL to 10 mL, from 0.5 mL to 5 mL, or from 0.5 mL to 2 mL.

The coronavirus proteins and antigens may be prepared from coronavirus infected cells. In certain embodiments, the method comprises preparing the proteins and antigens from a population of the cells prepared by in vitro and in vivo methods. For the in vitro method, VERO cells are cultured, and the cells are harvested following an infection of coronavirus.

IV. Compositions and Applications

Disclosed herein are embodiments of a composition comprising the isolated coronavirus proteins and/or antigens prepared according to embodiments of the disclosed method. While a person of ordinary skill in the art will appreciate that certain disclosed embodiments of the method concern isolating proteins and/or antigens from cells and/or culture media, the proteins and/or antigens are not necessarily purified. Thus, the composition may further comprise cell fragments, the extracting detergent, virus-infected cell lysate, or a combination thereof. The composition is suitable for use for any purpose for which coronavirus proteins and/or antigens are used. Non-limiting examples of applications of the proteins and/or antigens include the preparation of antibodies against the proteins/antigens; using the proteins and/or antigens as reference markers for coronavirus proteins; and using the proteins and/or antigens in an immunogenic composition, such as in a vaccine formulation, typically with a suitable adjuvant and optionally with a suitable carrier, and/or excipient. The immunogenic composition may be administered to a subject, such as an animal, particularly a porcine anime, to generate an immune response. Additional non-limiting examples of the compositions include those where the protein(s)/antigen(s) is/are in soluble or lyophilized (freeze dried) form.

The disclosed immunogenic composition has a different composition to that of a conventional coronavirus vaccine, including a conventional PEDV or PDCoV vaccine, such as a killed or attenuated vaccine. Embodiments of the disclosed method isolate infected cells containing the coronavirus proteins and antigens away from the supernatant, which contains the culture medium, at a time point substantially before viral particles have been released into the culture medium. Any viral particle that have been released into the culture medium are removed with the supernatant. The coronavirus proteins and antigens are then released from the infected cells by a suitable separation technique, such as extracting and/or eluting, freeze/thawing, or other techniques. In some embodiments, the infected cells may be lysed to release the coronavirus proteins and antigens. Any viral particles also released from the infected cells are inactivated, such as by a detergent and/or other inactivating agent. In some embodiments, the detergent is a detergent that is also used to extract and/or elute the proteins and antigens from the infected cells. In other embodiments, the inactivating agent is affirmatively added to the proteins and antigens. Thus, the composition made by the method comprises a high concentration of proteins produced by the infected cells and/or by the virus while within an infected cell, but a low concentration of actual viral particles.

This is in contrast to a killed vaccine, which typically is prepared by allowing the virus to carry the cell infection through the cytopathic effect (CPE) to substantial release of viral particles. Without being bound to a particular theory, the proteins produced by the infected cells and/or by the virus while within an infected cell may be useful for production of the viral particles, but are not necessarily properly exposed to the animal's immune system.

Therefore, the composition and concentration of the proteins and antigens included in the present immunogenic composition is very different from those found in killed or attenuated coronavirus vaccines.

In some embodiments, the immunogenic composition comprises, consists essentially of, or consists of, coronavirus proteins and antigens prepared by the disclosed method, a buffer solution, an adjuvant, an inactivating agent and a neutralizing agent. In certain embodiments, the buffer is PBS with EDTA, the inactivating agent is BEI, and/or the neutralizing agent comprises thiosulfate, such as sodium thiosulfate. In particular embodiments, the adjuvant is an oil-in-water adjuvant, such as an EMULSIGEN®-based adjuvant, or an adjuvant that adheres to the mucosal membranes, such as an adjuvant comprising polyacrylic acid, typically an adjuvant comprising carbopol such as CARBIGEN™.

In some embodiments, the composition comprises PEDV proteins and/or antigens, and may comprise proteins and/or antigens from one or more strains of PEDV, such as from 1, 2, 3, 4, 5, 6, or more strains of PEDV. In some embodiments, the composition comprises PDCoV proteins and/or antigens, and may comprise proteins and/or antigens from one or more strains of PDCoV, such as from 2, 3, 4, 5, 6, or more strains of PDCoV. The composition may comprise proteins and/or antigens from one or more species of coronavirus, such as from 1, 2, 3, 4, 5, 6, or more species of coronavirus, and each species of coronavirus in the composition independently may comprise 1, 2, 3, 4, 5, 6 or more strains of that particular species.

In certain embodiments concerning PEDV, strains suitable for use in the composition include any strain of PED virus, such as strains from North America, Europe and Asia. In particular embodiments, the PEDV strain is a Genogroup 2 strain, and may be a North American strain. In some embodiments, the disclosed immunogenic composition comprises PEDV proteins and antigens encoded by a PEDV strain having at least 90% identity (i.e., 90%, 91%, 92%, 93%, or 94%, or 95%, 96%, 97%, 98%, 99%, 99.1%, 99.2%, 99.3%, 99.4%, 99.5%, 99.6%, 99.7%, 99.8%, 99.9%, or 100%) to SEQ ID NO: 1, SEQ ID NO: 2, SEQ ID NO: 3, SEQ ID NO: 4, SEQ ID NO: 5, or SEQ ID NO: 6. In certain embodiments, the PEDV has at least 99%, 99.9% or 99.99% identity to SEQ ID NO: 1, SEQ ID NO: 2, SEQ ID NO: 3, SEQ ID NO: 4, SEQ ID NO: 5, SEQ ID NO: 6. Exemplary strains include, but are not limited to, the original US PEDV strain, Colorado 2013 (SEQ ID NO: 1), Iowa/18984/2013 (SEQ ID NO: 2), North Carolina USA/NC/2013/35140 (SEQ ID NO: 3), Indiana12.83/2013 (SEQ ID NO: 4), Iowa/2013 (SEQ ID NO: 5), 1251-125-10 (SEQ ID NO: 6), SM98 (SEQ ID NO: 7), KR-DR13-att (SEQ ID NO: 8), the INDEL strain, the S2aa-del strain, CV777, Chinese PEDV strains such as Chinese CH/ZMDZY/11, and AH2012 (SEQ ID NO: 9).

In certain embodiments concerning PDCoV, strains suitable for use in the composition include any strain of PDCoV virus, such as strains from North America, Europe and Asia. In particular embodiments, the PDCoV strain is a North American, Chinese, Korean or Thai strain. In some embodiments, the disclosed immunogenic composition comprises PDCoV proteins and antigens encoded by a PDCoV strain having at least 90% identity (i.e., 90%, 91%, 92%, 93%, or 94%, or 95%, 96%, 97%, 98%, 99%, 99.1%, 99.2%, 99.3%, 99.4%, 99.5%, 99.6%, 99.7%, 99.8%, 99.9%, or 100%) to at least one of SEQ ID NOS: 18-63. In certain embodiments, the PDCoV has at least 99%, 99.9% or 99.99% identity to at least one of SEQ ID NOS: 19-51.

The composition may comprise proteins and/or antigens from at least one additional pathogen. The additional pathogen may be any pathogen that causes illness and/or an infection in a porcine subject. Exemplary pathogens include, but are not limited to, porcine reproductive and respiratory syndrome virus (PRRSV), *Mycoplasma hyopneumoniae, Mycoplasma hyosynoviae, Mycoplasma rhinitis, Clostridium tetani, Clostridium perfringens*, porcine parvovirus, *Erysipelothrix rhusiopathiae, Leptospira pomona, Leptospira grippotyphosa, Leptospira hardjo, Leptospira canicola, Leptospira icterohaemorrhagiae, Leptospira bratislava*, porcine circovirus, *Lawsonia intracellularis, Escherchia coli, Actinobacillus pleuropneumoniae, Haemophilus parasuis, Salmonella choleraesuis, Salmonella typhimurium, Streptococcus suis, Pasteurella multocida, Bordetella bronchiseptica, Actinobacillus pleuropneumoniae, Serpulina hyodysenteriae*, encephalomyocarditis virus, swine influenza virus, transmissible gastroenteritis virus (TGE), swine delta coronavirus, rotavirus diarrhea, foot and mouth disease virus, classical swine fever virus, pseudorabies virus, Japanese encephalitis virus (JEV), encephalomyocarditis virus, or a combination thereof. In certain embodiments, the additional pathogen is not *Mycoplasma hyopneumoniae*. In other embodiments, the additional pathogen is *Clostridium tetani, Clostridium perfringens*, porcine parvovirus, *Erysipelothrix rhusiopathiae, Leptospira pomona, Leptospira grippotyphosa, Leptospira hardjo, Leptospira canicola, Leptospira icterohaemorrhagiae, Leptospira bratislava*, porcine circovirus, *Lawsonia intracellularis, Escherchia coli, Actinobacillus pleuropneumoniae, Haemophilus parasuis, Salmonella choleraesuis, Salmonella typhimurium, Streptococcus suis, Pasteurella multocida, Bordetella bronchiseptica, Actinobacillus pleuropneumoniae, Serpulina hyodysenteriae*, encephalomyocarditis virus, swine influenza virus, transmissible gastroenteritis virus (TGE), rotavirus diarrhea, foot and mouth disease virus, classical swine fever virus, pseudorabies virus, Japanese encephalitis virus (JEV), encephalomyocarditis virus, or a combination thereof.

In particular embodiments, the second pathogen is, or comprises, PRRSV. The PRRSV may comprise one or more North American strains, one or more European strains or combinations thereof. PRRSV strains may include, but are not limited to, Lelystad, VR2332 or HP-PRRSV. In certain embodiments, the PRRSV proteins and/or antigens are extracted or eluted by a method according to one or more of U.S. Pat. Nos. 7,241,582, 7,449,296, 7,776,537 or 8,142,788.

In some embodiments, an immunogenic composition as disclosed herein may comprise coronavirus proteins and/or antigens from one or more coronavirus species and/or strains, and proteins and/or antigens from one or more additional pathogens. In certain embodiments, the additional pathogen comprises PRRSV.

Also disclosed herein are combinations of immunogenic compositions, comprising at least one coronavirus immunogenic composition and at least one immunogenic composition directed toward a non-coronavirus porcine pathogen. In certain embodiments, the additional pathogen is or comprises PRRSV. In particular embodiments, the PRRSV immunogenic composition is an immunogenic composition prepared according to the methods disclosed in one or more of U.S. Pat. Nos. 7,241,582, 7,449,296, 7,776,537 or 8,142,788.

The immunogenic compositions in the combination of immunogenic compositions may be administered sequentially in any order, or at substantially the same time. In some embodiments, the immunogenic compositions may be mixed to form a single administrable composition. In other embodiments, the immunogenic compositions are administered as separate formulations.

The immunogenic compositions disclosed herein may also be administered in combination with other therapeutic agents suitable for administration to the subject, such as antibiotics, antiviral agents, antifungal agents, antiparasitic agents, or combinations thereof.

V. Detection of Protective Antibodies Against PEDV

Disclosed herein are embodiments of a method of detecting protective antibodies against PEDV. Antibodies against PEDV spike proteins having a molecular weight between 180-kDa to 350-kDa provide immunological protection in livestock such as swine. Accordingly, certain disclosed embodiments provide an agent that binds the antibodies against 180-kDa to 350-kDa of porcine epidemic diarrhea virus (PEDV), or PEDV. The agent may be used in embodiments of a method, device, and/or kit for detecting the presence of the antibodies against 180-kDa to 350-kDa of PEDV spike protein in a biological fluid.

Thus, disclosed herein are embodiments of a method of detecting antibodies against 180-kDa to 350-kDa post translationally modified PEDV spike protein in a sample of a biological fluid from a subject, particularly but not necessarily a porcine subject, suspected of being infected with PEDV. The method comprises contacting the sample, or a diluted form thereof, with a binding agent that binds the antibodies against 180-kDa to 350-kDa of PEDV spike protein. The binding of the agent, or agents, to the antibodies against 180-kDa to 350-kDa of PEDV spike protein forms a complex that may be detected to indicate the presence of the antibodies against 180-kDa to 350-kDa of PEDV spike protein post translational variants, and thus the presence of a PEDV infection in the subject from which the sample was obtained.

The biological fluid may be any fluid in which antibodies against 180-kDa to 350-kDa of PEDV spike protein post translational variants may be present in detectable amounts. Non-limiting examples include bodily secretions, such as saliva, tears, mucous, nasal discharge, and vaginal secretions as well as other bodily fluids such as blood, serum, plasma, semen, seminal fluid, milk, and urine as well as any fluid component of feces or a fluid extract of feces.

The binding agent which binds the antibodies against 180-kDa to 350-kDa of PEDV spike protein may be the spike protein, a 180-kDa to 350-kDa of PEDV spike protein post translational variants, or derivative thereof. In particular, binding agents may also be used to immobilize the antibodies against 180-kDa to 350-kDa of PEDV spike protein, or a macromolecular complex containing it, to facilitate its detection.

Also contemplated are labeled forms of the binding agent to facilitate its detection when bound to antibodies against 180-kDa to 350-kDa of PEDV spike protein. The binding agent may be labeled to permit direct detection, such as by conjugation to a label which is visible to the eye upon sufficient aggregation. Alternatively, the binding agent may be labeled for indirect detection, such as by conjugation to an enzyme, which is detected based upon its activity on a detectable substrate or to produce a detectable product. The binding agent may also be unlabeled and then detected based upon use of a detectable reagent, which binds the binding agent after formation of the complex. As a non-limiting example with the use of an antibody as the binding agent, the antibody complex comprising antibodies against 180-kDa to 350-kDa of PEDV spike protein post translational variants may be detected by a detectably labeled secondary antibody which binds the antibody bound to the antibodies against 180-kDa to 350-kDa of PEDV spike protein.

In another embodiment, detecting the binding agent complex is facilitated by immobilization of the complex. In some embodiments, the complex is immobilized to a solid substrate comprising an immobilized second binding agent which binds and immobilizes the complex. A first non-limiting example of such an embodiment comprises using a second binding agent to localize the complexes in discrete areas of the substrate to improve detection.

In another non-limiting embodiment, immobilization forms a "sandwich" wherein antibodies against 180-kDa to 350-kDa of PEDV spike protein are "sandwiched" between the binding agent and a second agent immobilized on a solid substrate which also binds antibodies against 180-kDa to 350-kDa of PEDV spike protein. As a non-limiting example, the complex may be immobilized by binding to a second binding agent immobilized to a solid substrate, such as a surface of a well, plate, dish or tube. The complex may then by detected based on localization on the surface. Alternatively the solid substrate may be a bead or chromatographic media which permits detection based on localization on the bead or media. The second binding agent preferably binds the antibodies against 180-kDa to 350-kDa of PEDV spike protein and the binding agent as described herein. Alternatively, the second binding agent is the same as the binding agent.

Also disclosed are embodiments of a device for practicing the above described method. Generally, such devices are useful for detecting the presence of antibodies against 180-kDa to 350-kDa of PEDV spike protein in a sample of a biological fluid as an indicator of PEDV infection in the subject from which the sample was taken. Thus the devices may be used as a rapid means of diagnosing the presence of PEDV infection.

The test strip may be uniform in composition, such as by being a unitary membrane strip comprising the first and second portions as described herein. Non-limiting examples include a strip of nitrocellulose membrane of appropriate pore size. Non-limiting examples of pore sizes include those in the range of 1-250 microns. Other non-bibulous materials may also be used, along with one or more mobilization agent as described herein to improve the mobilization of a dried first binding agent (the detector agent or preferably the detector antibody). Non-limiting examples of a mobilization reagent include glazes comprising sugar and/or BSA (bovine serum albumin).

Alternatively, the test strip is non-unitary in construction but the different components are functionally linked to permit fluid communication therebetween. In some embodiments, the first portion of the test strip as defined herein is composed of a porous or bibulous material. Non-limiting examples include cellulose or glass wool.

Placement of the first binding agent in a mobilizable form on the first portion of a device of the invention is preferably by drying a solution containing the agent thereon. In some embodiments, the solution is sprayed on and then dried prior to use. A non-limiting representative example of such a solution is one containing a detector reagent of the invention. Preferably, the first binding agent is labeled as described herein, such as with colloidal gold as a non-limiting example. In other embodiments, the test strip is within a housing or casing comprising liquid impermeable material to facilitate the manipulation and use of the test strip.

The test strip may be designed to operate solely based on the liquid available from a sample applied thereto (see for example U.S. Pat. No. 5,591,645 for analogous test strip embodiments). Alternatively, the test strip may be designed to operate in connection with a solvent or developing solution which increases the volume of the sample applied to the test strip (see for example U.S. Pat. No. 4,235,601 for analogous embodiments). In other embodiments, the test strip is embodied in a housing or casing, preferably composed of a plastic, polyacrylate or other liquid resistant material, to form a device of the invention. The test strip may include a backing composed of similar materials.

A test strip or other device of the invention may also comprise a control site or control region as described herein. The control site or region may comprise a reagent that produces a color upon being wetted. Non-limiting examples include cobalt chloride, copper chloride, and the like. Alternatively, the reagent may be a pH indicator which exhibits a color at the pH of the traversing fluid different from the color in the dry state. In a further alternative, the reagent is one that binds, and thus permits the detection of, a labeled first binding agent regardless of whether it has bound antibodies against 180-kDa to 350-kDa of PEDV spike protein.

The device may comprise both a first binding agent which binds antibodies against 180-kDa to 350-kDa of PEDV spike protein to form a complex and a second binding agent which immobilizes the complex. The first binding agent may thus be viewed as a "detector agent" and is as described herein. Where the first binding agent is 180-kDa to 350-kDa of PEDV spike protein, it may be viewed as a "detector antigen." The first binding agent may be located in a mobilizable form on a first portion of the device. A non-limiting example of how to make such a mobilizable first binding agent comprises drying the agent on a first portion of a device. Upon hydration with a liquid, such as a sample of a biological fluid, the agent is mobilized within the sample and thus may move with the liquid. Where the liquid, such as a sample of a biological fluid, contains antibodies against 200-kDa to 350-kDa of PEDV spike protein, the first binding agent binds the antibodies against 180-kDa to 350-kDa of PEDV spike protein to form a complex which moves with the liquid.

A second binding agent is immobilized on a second portion of a device to bind and immobilize a complex comprising the first binding agent and antibodies against 180-kDa to 350-kDa of PEDV spike protein when such a complex contacts the second binding agent. The second binding agent may thus be viewed as the "capture agent," or in the case of an antigen as the second binding agent, a "capture antigen." Contact between the second binding agent and the complex occurs via the movement of a liquid containing the complex, such as a sample of a biological fluid that contains a complex of antibodies against 180-kDa to 350-kDa of PEDV spike protein and mobilized first binding agent as described above, into contact with the second binding agent. Such movement is readily accomplished by the first and second portions of the device being in fluid communication with each other such that fluid in the first portion will move into and through the second portion. Such fluid communication may be direct, with no intervening material between the first and second portions, or indirect, with an intervening material between the first and second portions that permits liquid to pass from the first to second portions.

Detection of immobilized complex in the device, preferably by detection of a detectably labeled first binding agent immobilized in the second portion as permitted by the device, may be used to indicate the presence of antibodies against 180-kDa to 350-kDa of PEDV spike protein in a sample of biological fluid. The presence of antibodies against 180-kDa to 350-kDa of PEDV spike protein may be used as an indication of PEDV infection in the subject from which the sample was obtained. The sample is preferably from a porcine subject, or other subject suspected of being infected with PEDV, but any subject which may be infected by PEDV carrier may be used in the devices of the invention.

Biological fluids that may be used in the device include any fluid in which antibodies against 180-kDa to 350-kDa of PEDV spike protein may be detectably present. Non-limiting examples have been provided above and below, and dilutions of such fluids may also be used as the sample.

The present disclosure provides a binding agent capable of binding antibodies against 180-kDa to 350-kDa of PEDV spike protein in a sample of a biological fluid from a subject. Preferably, the binding agent specifically binds 180-kDa to 350-kDa of PEDV spike protein antibodies to the exclusion of other molecules present in the biological fluid. In many embodiments of the disclosure, the subject is a pig, and thus the sample may be of a bodily fluid or secretion from a pig. Non-limiting examples of pigs from which samples may be obtained for use with the present invention include boar, sow, fattener, gilt, nursery pigs, finishing pigs, and weaned pigs. The pigs may range in age from 1 day to at least 60 days, such as from 1 day to about 30 days, 30 days to about 40 days, 41 days to about 50 days, or 51 days to about 60 days or older.

The binding agent preferably, or substantially selectively, binds an antibody against 180-kDa to 350-kDa of PEDV spike protein as found in multiple PEDV strains and isolates. In other embodiments, the binding agent does not cross react with other porcine viruses, such as circovirus, porcine parvovirus (PPV), Japanese encephalitis virus (JEV), rotavirus, pseudorabies, encephalomyocarditis virus, swine influenza virus, PRRSV or transmissible gastroenteritis (TGE) virus.

The binding agent is preferably a 180-kDa to 350-kDa of PEDV spike protein, or a fragment thereof, which binds 180-kDa to 350-kDa of PEDV spike protein antibodies. Accordingly, the disclosure provides an immunochromatographic-based method for detecting PEDV. FIG. 6 provides a Western blot illustrating detection of antibodies against 180-kDa to 350-kDa of PEDV spike protein. With reference to FIG. 6, pigs in cases 1 and 2 maintained healthy status without diarrhea, but pigs in cases 3 and 4 had severe diarrhea caused by PEDV.

The 180-kDa to 350-kDa of PEDV spike protein may be generated by any appropriate method known in the art. Suitable methods include, but are not limited to recombinant, extraction, and/or synthetic methods.

As explained herein, the binding agent may be labeled to facilitate its detection, such as, for example, by attachment to another moiety. The moiety is preferably a detectable label, including a directly detectable label, such as a radioactive isotope, a fluorescent label (Cy3 and Cy5 as non-limiting examples) or a particulate label. Non-limiting examples of particulate labels include latex particles, metal sols, and colloidal gold particles. Alternatively, the label may be for indirect detection. Non-limiting examples of labels suitable for indirect detection include an enzyme, such as, but not limited to, luciferase, alkaline phosphatase, and horse radish peroxidase. Other non-limiting examples include a molecule bound by another molecule, such as, but not limited to, biotin, an affinity peptide, or a purification tag. Preferably, the label is covalently attached.

The binding agent may be used to detect antibodies against 180-kDa to 350-kDa of PEDV spike protein in a sample of a biological fluid from a subject as described herein. The sample is preferably from an individual suspected of being infected with PEDV due to the presence of symptoms indicative of an infection. Alternatively, embodiments of the disclosed method may be used as part of routine screening of animals, such as those of a farm to permit rapid identification and isolation of infected individuals. Certain embodiments also may be used in specific instances, such as prior to transport or transfer of an animal from one location to another to permit identification of infection and prevent spread of infection.

Also disclosed herein are embodiments of a kit comprising a binding agent, or a composition and/or device comprising the binding agent, for use in one or more embodiments of the method disclosed herein. Such kits optionally further comprise an identifying description or label or instructions relating to their use in the methods of the present invention. Such a kit may comprise containers, each with one or more of the various reagents (typically in concentrated form) or devices utilized in the methods. A set of instructions will also typically be included.

Embodiments of a kit comprising a device may further comprise one or more additional reagents or pieces of equipment for use with the device. Non-limiting examples of additional materials for inclusion are sample diluent solution, diluent vial, and a dropper for transfer of sample.

IV. Examples

Example 1

Preparation of PEDV Proteins and/or Antigens

PEDV proteins may be prepared from a PEDV strain by infecting susceptible cells in vitro or in vivo, and harvesting the infected cells at an optimal time to prepare cell-associated viral components. For in vitro methods, the antigen(s) may be prepared by a cell culture system or by using recombinant technologies.

In an exemplary embodiment, MARC cells were pelleted by centrifugation, and the supernatant was removed or discarded. The pellets may be optionally washed. PEDV proteins and antigens were extracted from the cell pellets by suspending the cell pellets in a 0.05M tris (hydroxymethyl) aminomethane 0.025M EDTA buffer containing 0.5% Triton X-100 at a volume of 5-10 times that of the packed cells. The mixture was stirred for 2-15 hours at 4° C. and then centrifuged at 10,000 g for 1 hour. In another example, the mixture was stirred for 0.5-10 hours at 4-25° C. and filtered to remove cell debris.

The resulting supernatant comprised the PEDV proteins and antigens. Optionally, the antigen-containing solution may then undergo one or more freeze-thawing cycles, one or more of each, followed by an additional extraction cycle, to further break up intact cells and increase the efficiency of the extraction process. The freeze-thawing process also may facilitate ensuring that the antigen solution is non-infectious and allowing its use without a risk of spreading the virus.

FIG. 1 provides a photograph of a Western blot of PEDV proteins. The proteins were obtained from infected cells by an exemplary embodiment of the disclosed method and were mixed with one of two monoclonal antibodies, 6C8 or 3F12, which were selected to detect certain PEDV proteins. Lanes identified as 'S' contained pre-stained protein molecular weight markers. The other lanes contained samples from a PEDV infected cell culture medium at the end of culture (lanes 1), an extract of isolated PEDV infected cells diluted 2× (lanes 2), an extract of isolated PEDV infected cells diluted 3× (lanes 3), an extract of isolated PEDV infected cells diluted 4× (lanes 4), and an extract of isolated PEDV infected cells diluted 5× (lanes 5). Surprisingly, in this example, both of the monoclonal antibodies used appeared to detect proteins with the same molecular weight.

Figure 2:
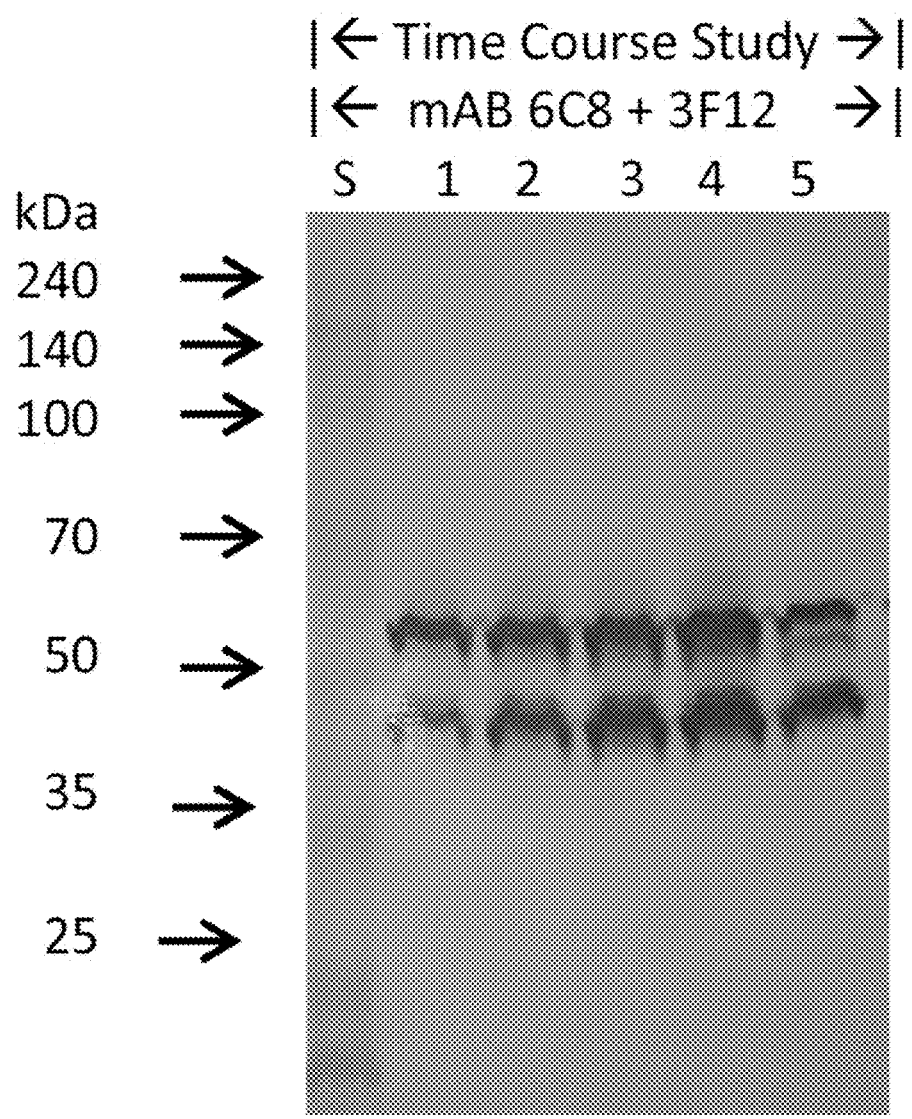
FIG. 2 is a Western blot of PEDV proteins from cultures of infected cells over time, with a mixture of the two monoclonal antibodies used in FIG. 1.

FIG. 2 provides a photograph of a Western blot of PEDV proteins from cultures of infected cells over time with a mixture of the two monoclonal antibodies used in FIG. 1. Lane S contained pre-stained protein molecular weight markers. The other lanes contained extracted samples from isolated PEDV infected cells 24 hours post infection (lane 1), 30 hours post infection (lane 2), 35 hours post infection (lane 3), 47 hours post infection (lane 4), and 52 hours post infection (lane 5).

The results from these two experiments demonstrated that the disclosed method successfully extracted proteins from cells infected with PEDV. Moreover, the Western blots illustrate that the extraction method results in a concentrated mixture of proteins compared to a culture medium, such as the culture medium of a killed virus vaccine. The concentration of proteins in the extracts or eluents may be more than twice the concentration of proteins in the culture medium, such as 4 times, 6 times, 8 times, 10 times or more than 10 times the concentration of proteins in the culture medium.

Example 2

Vaccine Preparation Comprising PEDV Proteins and/or Antigens

A vaccine was prepared using the method described in Example 5 from an exemplary antigen solution prepared by the disclosed method. The vaccine was administered to sows at 3-5 days pre-farrow in an endemic herd, 150 days post clinical break. FIG. 3 shows the data from a test where the vaccinated and non-vaccinated sows were kept in the same room. FIG. 4 shows data from a test where vaccinated and non-vaccinated sows were kept in separate rooms. The piglet mortality rates in FIGS. 3 and 4 are 15% and 9.6%, respectively, for piglets from the vaccinated sows, compared to 28% and 17.6%, respectively, for piglets from non-vaccinated sows. FIG. 5 provides baseline data from non-vaccinated herds from multiple farms, illustrating the pre-wean mortality based on days post initial whole herd PEDV virus exposure. The data in FIGS. 3-5 clearly illustrates the efficacy of the exemplary vaccine prepared by the disclosed method.

Example 3

Preparation of Porcine Deltacoronavirus Proteins and/or Antigens

Porcine deltacoronavirus (PDCoV) proteins and/or antigens may be prepared from a PDCoV strain by infecting susceptible cells in vitro or in vivo, and harvesting the infected cells at an optimal time to prepare cell-associated viral components. For in vitro methods, the antigen(s) may be prepared by a cell culture system or by using recombinant technologies.

Cells are pelleted by centrifugation, and the supernatant is removed or discarded. The pellets may be optionally washed. Porcine delta coronavirus proteins and antigens are extracted from the cell pellets by suspending the cell pellets in a buffer, such as 0.05M tris (hydroxymethyl) aminomethane 0.025M EDTA buffer containing 0.5% Triton X-100 at a volume of 5-10 times that of the packed cells. The mixture is stirred for 2-15 hours at 4° C. and then centrifuged at 10,000 g for 1 hour. The resulting supernatant comprises the PDCoV proteins and antigens. Optionally, the antigen-containing solution may then undergo one or more freeze-thawing cycles, one or more of each, followed by an additional extraction cycle, to further break up intact cells and increase the efficiency of the extraction process. The freeze-thawing process also may facilitate ensuring that the antigen solution is non-infectious and allowing its use without a risk of spreading the virus.

Example 4

PEDV proteins may be prepared from a PEDV strain by infecting susceptible cells in vitro or in vivo, and harvesting the infected cells at an optimal time, typically from 24 to 60 hours post infection, to prepare cell-associated viral components. For in vitro methods, the antigen(s) may be prepared by a cell culture system or by using recombinant technologies.

In an exemplary embodiment, the supernatant containing whole virus particles was poured off from the cells and removed or discarded. The cells may optionally be washed. PEDV proteins and antigens were extracted from the cell by suspending the cell pellets in a 0.05M tris (hydroxymethyl)

aminomethane 0.025M EDTA buffer containing 0.5% Triton X-100 at one fifth to one eighth volume of culture supernatant volume. The cells were incubated with the buffer for 20 minutes to 1 hour at room temperature (25° C.) and then optionally frozen. The resulting extract comprised the PEDV proteins and antigens. Optionally, the antigen-containing solution may then undergo one or more freeze-thawing cycles, followed by an additional extraction cycle, to further break up intact cells and increase the efficiency of the extraction process. The freeze-thawing process also may facilitate ensuring that the antigen solution is non-infectious and allowing its use without a risk of spreading the virus. The freeze-thawed solution may be filtered or centrifuged to remove cell debris. After this extraction process it was found that the proteins and antigens were inactivated. Optionally, an inactivating agent such as binary ethyleneimine is added to insure inactivation.

Example 5

Vaccine Preparation

Detergent extracts (DE samples) were prepared from MARC (monkey kidney) cells infected with Colorado (CO), Iowa (IA), and North Carolina (NC), SEQ ID NO: 1, SEQ ID NO: 2, and SEQ ID NO: 3, respectively (FIGS. 7-9). FIG. 7 is a Western blot of the detergent extracts. For each extract, 2×, 3×, and 4× diluted samples were run (lanes 1-3, respectively). A sample of each full grown virus culture also was run (lane 4).

The three DE samples were mixed in equal volume to make 1,000 mL to form a DE mixture. The DE mixture was inactivated with binary ethyleneimine (BEI) and neutralized with sodium thiosulfate. The resulting solution had a volume of about 1,200 mL. Samples taken before and after the inactivation process were tested to confirm that there was no live virus in the DE mixture after the inactivation process. FIG. 8 is a Western blot of the three DE extracts (lanes 1-3), the DE mixture before inactivation (lane 4), the DE mixture after inactivation (lane 5), and a mixture of the three viral cultures in equal volume.

The inactivated DE mixture was split into two parts –850 mL (Part A) and 350 mL (Part B). Part A was diluted with PBS (650 mL) and mixed with 300 mL of Emulsigen-D adjuvant (Phibro Animal Health Corporation, Omaha, Nebr., USA) to form an intramuscular (IM) vaccine (2 mL/dose). Part B was not diluted and was mixed with 70 mL of CARBIGEN™ adjuvant (Phibro Animal Health Corporation, Omaha, Nebr., USA) to form an intranasal (IN) vaccine (1 mL/dose). Each mixture was blended with an industrial grade blender (Commercial Blender 7011, Model 31BL92, Dynamic Corporation of America, New Hartford, Conn.). The blended solution was aliquoted into 50 mL batches for IM vaccine or 20 mL batches for IN vaccine, and stored until use. In trials, the IN vaccine was also used as a subcutaneous (SQ) vaccine.

Example 6

Pre-Wean Mortality in Vaccinated and Unvaccinated Pigs

Table 1 shows multiple farm examples of pre-wean mortality based on days post initial whole herd PEDV exposure. The data was used as a baseline to compare vaccine performance.

TABLE 1

| Days post exposure | Farm 1 | Farm 2 | Farm 3 | Farm 4 | Farm 5 | Farm 6 | All farm average |
|---|---|---|---|---|---|---|---|
| 1-7 | 100 | 99 | 97 | 100 | 97 | 100 | 98% |
| 8-15 | 98 | 94 | 98 | 98 | 100 | 100 | 98% |
| 16-23 | 51 | 47 | 78 | 89 | 90 | 100 | 76% |
| 24-31 | 23 | 24 | 34 | 54 | 45 | 100 | 46% |
| 32-39 | 19 | 14 | 27 | 43 | 34 | 100 | 39% |
| 40-47 | 19 | 25 | 17 | 30 | 16 | 22 | 21% |
| 48-55 | 24 | 12 | 18 | 27 | 20 | 37 | 23% |
| 56-63 | 19 | 11 | 16 | 25 | 19 | 32 | 20% |
| Individual farm average prior to PEDV | 15% | 14% | 15% | 20% | 17% | 12% | |

In one trial sows received the PEDV vaccine 3-5 days pre-farrow (endemic infection, 150 days post clinical break). Treated and non-treated litters were in the same room. Table 2 summarizes the results.

TABLE 2

| | Born alive | Pigs remaining at weaning | Piglet mortality |
|---|---|---|---|
| Vaccinated sows - 10 head, 2 cc dose | 133 (13.3 avg.) | 113 (11.3 avg.) | 15% |
| Non-vaccinated sows, 33 head | 405 (12.2 avg.) | 291 (8.8 avg.) | 28% |

In another trial, sows received the vaccine at 3-5 days pre-farrow (1 cc dose) in an endemic herd (150 days post clinical break) where all litters within a room were vaccinated or non-vaccinated. The results are shown in Table 3.

TABLE 3

| | # of litters | Born alive | Pigs weaned | Pre-wean mortality |
|---|---|---|---|---|
| Entire room vaccinated | 128 | 1466 (11.4 avg.) | 1324 (10.3 avg.) | 9.6% |
| No vaccine used in room | 88 | 1059 (12.0 avg.) | 872 (9.9 avg.) | 17.6% |

In another trial, nursing piglets were vaccinated intranasally between 2-4 days of age (endemic farm, 150 days post clinical break). Table 4 summarizes the results.

TABLE 4

| | Vaccinated nursing piglets (1 cc dose) | Non-vaccinated nursing piglets |
|---|---|---|
| # of litters exhibiting clinical scour | 5 of 15 litters (33%) | 8 of 27 litters (30%) |
| # of litters where all pigs died | 0 of 15 litters (0%) | 5 of 27 litters (18%) |
| Piglet mortality | 22% | 44% |
| Piglet morbidity | 12% | 13% |

In another trial, PEDV vaccine was administered intramuscularly to nursing piglets in an endemic herd (150 days post clinical break). The results are shown in Table 5.

TABLE 5

| | Born alive | Pigs remaining at weaning | Pre-wean mortality |
|---|---|---|---|
| Nursing piglets 1 cc IM, 2-3 days old, 7 litters | 79 (11.2 avg.) | 60 (8.6 avg.) | 24% |
| Nursing piglets 2 cc IM, 2-3 days old, 7 litters | 81 (11.5 avg.) | 72 (10.3 avg.) | 11% |
| Nursing piglets no vaccine | 265 (11.0 avg.) | 191 (7.9 avg.) | 28% |

In another trial, PEDV vaccine was administered to PEDV naïve isowean pigs at weaning on Day 0. Vaccines were administered subcutaneously (SubQ), intramuscularly (IM), or intranasally (IN). The pigs were weighed and given a booster vaccine on Day 21. The pigs were challenged and weighed on Day 45, and weighed again on Day 56. The results are shown in Table 6.

TABLE 6

| Group | Wean weight and 1st vaccination (Day 0) | Booster vaccination weight (Day 21) | Day of challenge weight (Day 45) | End weight (Day 56) |
|---|---|---|---|---|
| Controls (red tags) | 12.9 | 24.9 | 44.6 | 54.1 |
| SubQ vaccination (green tags) | 13.6 | 23.5 | 50.8 | 61.3 |
| IN vaccination (pink tags) | 13.3 | 27.8 | 51.0 | 66.6 |
| IM vaccination (purple tags) | 13.4 | 27.4 | 48.8 | 68.0 |

Table 7 shows the average daily gain for days 1-45 post vaccination and days 1-11 post challenge.

TABLE 7

| Group | ADG Days 1-45 post vaccination | ADG Days 1-11 post challenge |
|---|---|---|
| Controls (red tags) | 0.71 | 0.85 |
| SubQ vaccination (green tags) | 0.83 | 0.95 |
| IN vaccination (pink tags) | 0.84 | 1.41 |
| IM vaccination (purple tags) | 0.79 | 1.75 |

Fecal shedding was evaluated 11 days post challenge in naïve isowean pigs. The values shown in Table 8 are PCR cycle times (CT) values. The lower the number, the higher the level of viral material in the sample. The negative cut-off is 35.

TABLE 8

| Group | Average CT value | Range in CT values |
|---|---|---|
| Controls | 28.3 | 21.9-33.0 |
| SubQ vaccination | 32.8 | 30.0-33.1 |
| IN vaccination | 26.2 | 21.3-30.0 |
| IM vaccination | 32.4 | 31.2-34.7 |

In another trial, the disclosed vaccine (MJ PEDV) was evaluated against a commercial PEDV vaccine in an endemic farm 150 days post clinical break. The vaccines were administered 3-5 days pre-farrow. The results are summarized in Table 9. The data is a composite of three farrowings in which all three groups were scattered throughout rooms.

TABLE 9

| | # of litters | Born alive | Pigs remaining | Pre-wean mortality |
|---|---|---|---|---|
| MJ PEDV 1 cc IM | 36 | 412 (11.4 avg.) | 357 (9.9 avg.) | 13.3% |
| Commercial PEDV 1 cc IM | 50 | 598 (11.9 avg.) | 458 (9.1 avg.) | 23.4% |
| Non-vaccinates | 33 | 422 (12.7 avg.) | 311 (9.4 avg.) | 26.3% |

In another trial, the disclosed vaccine (MJ PEDV) was evaluated against two commercial PEDV vaccines during an acute outbreak. Sows farrowed 9 to 22 days post PEDV whole herd feedback. The results are shown in Table 10.

TABLE 10

| Group treatment | Sow dosage of vaccine | Days farrowed post feedback exposure | Number of litters in group | Average born alive | Viable pigs remaining at 16 days of age | Pre-wean mortality |
|---|---|---|---|---|---|---|
| Controls | No vaccine | 9-21 days | 6 litters | 13.1 | 6.1 | 53.4% |
| Commercial vaccine 1 | 2 cc/2 cc | 10-22 days | 6 litters | 7.8 | 4.8 | 38.4% |
| Commercial vaccine 2 | 2 cc/2 cc | 9-21 days | 7 litters | 12.4 | 7.2 | 41.9% |
| MJ | 2 cc/2 cc | 12-22 days | 10 litters | 9.3 | 6.9 | 25.8% |

Example 7

PEDV Active Farm Trials

A farm experienced an outbreak of PEDV. After feeding back, the herd had stabilized. A few months after the initial outbreak, bringing in naïve gilts acclimated for PEDV caused a second PEDV event on the farm. The farm was farrowing 145-150 sows/week. Each farrowing room included 44 crates; each farrowing group occupied 3+ farrowing rooms.

Five litters in Room #1 may be selected at 5 days old (day zero). Each piglet may be given 1 mL of IN vaccine, and the immunized piglets may be marked. Mortality may be compared between vaccinated and unvaccinated litters at weaning during days 14-19.

Rooms 2-4 may include sows bred at the same time. Sows in Room #2 and half the sows in Room #3 may not be vaccinated. The remaining sows in Room #3 and the sows in Room #4 may be vaccinated with IM vaccine (2 cc/sow) on day zero. The sows may farrow on days 14-19. Five litters at 5 days old (days 21-26 post sow vaccine) may be selected from Room #4; the selected piglets may be immunized with 1 mL of IN vaccine and marked. On days 37-44 post sow vaccination, mortality may be compared at weaning among litters that receive no vaccine, litters in which the sows receive IM vaccine and the piglets are unvaccinated, and litters in which the sows receive IM vaccine and the piglets receive IN vaccine.

Rooms 5-7 may include sows bred at the same time. Sows in Room #5 and half the sows in Room #6 may not be vaccinated. The remaining sows in Room #6 and the sows in Room #7 may be vaccinated with IM vaccine (2 cc/sow) on day zero. The vaccinated sows may receive a booster vaccination 14-19 days post initial vaccination. The sows may farrow on days 28-34 post initial vaccination. Five litters at 5 days old may be selected from Room #7 on days 33-39; the piglets may be vaccinated with 1 mL of IN vaccine and marked. On days 47-53, mortality may be compared at weaning among litters that receive no vaccine, litters in which the sows receive IM vaccine and the piglets are unvaccinated, and litters in which the sows receive IM vaccine and the piglets receive IN vaccine.

Example 8

Comparison of Vaccination Protocols

Sows and/or piglets were immunized intramuscularly with 1-4 cc of PEDV vaccine. The piglets were monitored to determine the effect on mortality.

TABLE 11

Room 3

| Dose/ pig IM | # litters vacci- nated | Total pigs vacci- nated | Born alive per litter | Pigs wean vaccinated | Pigs weaned per litter | Piglet mortality |
|---|---|---|---|---|---|---|
| 1 cc | 7 | 79 | 11.2 | 60 | 8.6 | 24% |
| 2 cc | 7 | 81 | 11.5 | 72 | 10.3 | 11.1% |
| — | 24 | 265 | 11.0 | 191 | 7.9 | 28% |

One litter in the 1 cc group of pigs had severe scours.
Pigs were vaccinated at 1-2 days of age.
Pigs were weaned at 17-19 days of age.

TABLE 12

Room 4

| Dose/ pig IM | # sows vacci- nated | Born alive per litter | Pig inven- tory from vaccinated sows | Pig inven- tory at 15 days of age | Piglet mortality |
|---|---|---|---|---|---|
| 2 cc | 10 | 11.2 | 112 | 99 | 11.6% |
| — | 33 | 12.1 | 399 | 333 | 16.7% |

Sows were given vaccine between day of farrowing out to day 6 pre-farrow.
Average timing was 2.2 days pre-farrow for vaccinated sows.

TABLE 13

Room 5

| Dose/ pig IM | # sows vacci- nated | Born alive per litter | Pig inven- tory from vaccinated sows | Pigs remaining | Piglet mortality |
|---|---|---|---|---|---|
| 4 cc | 10 | 13.3 | 133 | 113 | 15% |

Example 9

Vaccination of PEDV Naïve Pigs

Forty PEDV naïve isowean pigs (20 days old) may be divided into 4 groups randomly and tagged (Groups A, B, C, and D). Four days later, each pig may be weighted and a blood sample obtained before vaccination. On day zero, Group A may receive 2 ml of a control vaccine, Group B may receive 2 mL of IM vaccine, Group C may receive 1 mL of IN vaccine (0.5 mL×2 spots), and Group D may receive 1 mL of SQ vaccine (0.5 mL×2 spots). On day 21, blood samples may be obtained and each pig may receive a booster vaccination. On day 34, the pigs may be moved to a new location. On day 35, a third blood sample may be obtained, and the pigs may be challenged by giving each pig 1 mL of "gut-homogenizer" by mouth. Each pig's behavior may be observed daily for two weeks. On day 41 (6 days post challenge), a fourth blood sample may be obtained. On day 45 (10 days post challenge), a fifth blood sample may be obtained.

Example 10

Vaccination of Sows Previously Exposed to PEDV

A PED stabilized farm may be selected. Sero-converting gilts may be kept by the PEDV-feedback method. $P_0$ sows may be identified in 4 groups—8, 6, 4, and 2 prefarrowing groups, 30 gilts per group (15 for control, and 15 for vaccination). Blood samples may be obtained before vaccination. Pigs may be vaccinated with 2 mL of IM vaccine; controls may receive PBS+adjuvant. Blood samples may be obtained before a booster vaccination (2 mL of IM vaccine) at 2, 3, or 4 weeks later.

TABLE 14

| | Group | | | |
|---|---|---|---|---|
| Day | I | II | III | IV |
| 0 | B, V | B, V | B, V | B, V |
| 7 | | | | |
| 14 | B, F | B, V | | |
| 21 | Observe piglet performance (OPP) | | B, V | |
| 28 | OPP | B, F | | B, V |
| 35 | OPP | OPP | | |
| 42 | OPP | OPP | B, F | |
| 49 | | OPP | OPP | |
| 56 | | | OPP | B, F |
| 63 | | | OPP | OPP |
| 70 | | | | OPP |
| 77 | | | | OPP |

B = blood sample,
V = vaccination,
F = farrowing

Example 11

PEDV proteins usable in vaccines may be prepared from a PEDV strain by infecting susceptible cells in vitro or in vivo, and harvesting the infected cells at an optimal time to prepare cell-associated viral components. For in vitro methods, the antigen(s) may be prepared by a cell culture system or by using recombinant technologies.

For instance, MARC cells can be grown in cell culture and infected with PEDV either with or without the addition of trypsin. The trypsin is added at a concentration that will help the virus infect the cells sheet without destroying the cells. For instance, at a concentration of 1-10 µg/mL. Once the cells show evidence of infection by the PEDV, the culture medium is removed and discarded. The cells may be optionally washed. A buffer such as Tris or phosphate buffered saline (PBS) with EDTA is added, swirling to coat the cell sheet and then the PEDV proteins and antigens are extracted by placing the culture vessels (roller bottles, flasks, beads or other types of matrix) with the buffer into a freezer at a temperature at or below −10° C. The vessels are allowed to freeze and then are thawed. Thawing breaks open the cells and releases the PEDV proteins and antigens useful for preparation of a vaccine. Optionally, the thawed culture may be refrozen and rethawed to release more proteins and antigens and optionally filtered or centrifuged to remove cell debris. After release of the proteins/antigens, an inactivating agent such as binary ethyleneimine (BEI), formalin, beta propiolactone (BPL) or any other effective inactivating agent is added while mixing. Mixing of the inactivating agent with the culture is continued until inactivation is complete, usually at least 30 minutes. After inactivation, the solution of viral protein and antigens may be diluted with proper buffer solution like PBS and excipients, and adjuvanted or adjuvanted without further dilution. Acceptable adjuvants include oil-in-water adjuvants such as those containing EMULSIGEN®, adjuvants comprising polymers such as those comprising acrylic acids or carbomers such as CARBIGEN™, or other types of polymers such as POLYGEN™. Once the antigens are inactivated and adjuvanted they may be administered to animals, preferably pigs, via intramuscular, subcutaneous, intranasal or oral routes.

Example 12

An autogenous immunogenic composition comprising coronavirus proteins and antigens is produced from a sample received from an infected subject. The subject may be a swine. The sample is analyzed to determine if it is infected with a coronavirus, and if so, to determine the species and strain of the virus. The virus is then replicated and the proteins and antigens isolated by the method disclosed herein to produce an immunogenic composition. Optionally, an adjuvant may be added to the composition. An autogenous immunogenic composition produced by the disclosed method is typically administered to one or more of: (1) the infected subject; (2) other subjects in an infected population that includes or included the infected subject; (3) subjects that may have or have had contact with the infected subject; or (4) subjects in close proximity to the infected subject, such as a neighboring building, field or farm.

Optionally, one or more coronavirus strains of the same species are identified and/or selected for the production of a combination immunogenic composition. Additionally, or alternatively, isolated proteins and antigens from one or more additional coronavirus species and/or non-coronavirus species may be included in the immunogenic composition. The additional strain(s) and/or species may be selected to produce an improved immune response in a subject when administered in combination with proteins and antigens from the received sample, selected based on prior and/or current infection history of the subject or the subject's location, selected to protect the subject from potential future infection, or any combination thereof.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10280199B2). An electronic copy of the "Sequence Listing" will also be available from the USPTO upon request and payment of the fee set forth in 37 CFR 1.19(b)(3).

We claim:

1. A method, comprising:
   isolating porcine epidemic diarrhea virus (PEDV)-infected cells away from cell-free PEDV viral particles in a population of cells in a culture medium;
   extracting or eluting PEDV proteins and antigens from the isolated PEDV-infected cells with a detergent-containing solution to form a first solution comprising detergent and isolated PEDV proteins and antigens; and
   adding an adjuvant to the first solution to form a second solution comprising the isolated PEDV proteins and antigens, the detergent and the adjuvant.

2. The method of claim 1, further comprising allowing the population of cells to incubate for a time period sufficient to result in one or more replicated PEDV viral particles being released into the culture medium.

3. The method of claim 1, wherein the detergent-containing solution comprises a non-ionic detergent.

4. The method of claim 3, wherein the non-ionic detergent is poly(ethylene glycol) p-isooctyl-phenyl ether, octylphenoxypolyethoxyethanol (Nonidet P-40), 4-(1,1,3,3-tetramethylbutyl)phenyl-polyethylene glycol (Triton X-100), or a combination thereof.

5. The method of claim 3, wherein the detergent-containing solution comprises a detergent at a concentration of greater than zero to 5% in solution.

6. The method of claim 3, wherein the detergent-containing solution comprises a chelating agent at a concentration of greater than zero to 0.5M in solution.

7. The method of claim 1, wherein extracting or eluting PEDV proteins and antigens comprises extracting or eluting PEDV proteins and antigens for about 0.1 to about 15 hours.

8. The method of claim 7, wherein extracting or eluting PEDV proteins and antigens is performed at a temperature of from 0° C. to 25° C.

9. The method of claim 7, wherein extracting or eluting PEDV proteins and antigens comprises extracting or eluting PEDV proteins and antigens for from 0.1 hours to 15 hours at 4° C.

10. The method of claim 1, wherein the proteins and antigens include PEDV envelope proteins.

11. The method of claim 1, wherein the first solution of isolated PEDV proteins and antigens has a concentration of PEDV proteins and antigens greater than a concentration of PEDV proteins and antigens in the culture medium that contained the population of infected cells.

12. The method of claim 1, further comprising adding an excipient to the first solution or the second solution.

13. A method, comprising:
isolating PEDV-infected cells away from cell-free PEDV viral particles in a population of cells in a culture medium;
allowing the population of cells to incubate for a time period sufficient to result in one or more replicated PEDV viral particles being released into the culture medium;

extracting or eluting PEDV proteins and antigens from the isolated PEDV-infected cells with a detergent-containing solution to form a solution of isolated PEDV proteins and antigens; and adding an adjuvant to the solution of isolated PEDV proteins and antigens, to form an immunogenic composition comprising PEDV proteins and antigens, cell fragments, the detergent and the adjuvant.

14. A composition comprising isolated PEDV proteins and antigens from claim 1, an adjuvant, and a detergent made by the method of claim 1.

15. The composition of claim 14, comprising PEDV proteins and antigens, cell fragments, the detergent and the adjuvant.

16. A method of vaccinating a subject, the method comprising administering to the subject the second solution from claim 1 or a composition comprising the second solution of isolated PEDV proteins and antigens from claim 1.

17. The method of claim 16, wherein the subject is a porcine subject.

18. A method of generating an immune response in a porcine subject, the method comprising administering to the subject the composition of claim 15.

19. The method of claim 6, wherein the chelating agent is ethylenediaminetetraacetic acid.

20. The composition of claim 14, wherein the composition comprises the isolated PEDV proteins and antigens, the adjuvant, the detergent, and ethylenediaminetetraacetic acid.

* * * * *